US009096644B2

(12) United States Patent
Tan et al.

(10) Patent No.: US 9,096,644 B2
(45) Date of Patent: *Aug. 4, 2015

(54) ANTIGEN-NOROVIRUS P-DOMAIN MONOMERS AND DIMERS, ANTIGEN NOROVIRUS P-PARTICLE MOLECULES, AND METHODS FOR THEIR MAKING AND USE

(71) Applicant: Children's Hospital Medical Center, Cincinnati, OH (US)

(72) Inventors: Ming Tan, Cincinnati, OH (US); Xi Jiang, Cincinnati, OH (US)

(73) Assignee: Children's Hospital Medical Center, Cincinnati, OH (US)

( * ) Notice: Subject to any disclaimer, the term of this patent is extended or adjusted under 35 U.S.C. 154(b) by 103 days.

This patent is subject to a terminal disclaimer.

(21) Appl. No.: 13/924,906

(22) Filed: Jun. 24, 2013

(65) Prior Publication Data
US 2013/0273090 A1    Oct. 17, 2013

Related U.S. Application Data

(63) Continuation of application No. 12/797,396, filed on Jun. 9, 2010, now Pat. No. 8,486,421.

(60) Provisional application No. 61/185,564, filed on Jun. 9, 2009, provisional application No. 61/224,696, filed on Jul. 10, 2009.

(51) Int. Cl.
| | |
|---|---|
| *C07K 7/06* | (2006.01) |
| *A61K 38/00* | (2006.01) |
| *A61K 39/12* | (2006.01) |
| *A61K 39/125* | (2006.01) |
| *C07K 5/10* | (2006.01) |
| *A61K 39/00* | (2006.01) |

(52) U.S. Cl.
CPC . *C07K 7/06* (2013.01); *A61K 38/00* (2013.01); *A61K 39/12* (2013.01); *A61K 39/125* (2013.01); *C07K 5/10* (2013.01); *A61K 2039/5258* (2013.01); *A61K 2039/542* (2013.01); *A61K 2039/543* (2013.01); *A61K 2039/55566* (2013.01); *A61K 2039/58* (2013.01); *A61K 2039/6075* (2013.01); *A61K 2039/645* (2013.01); *A61K 2039/70* (2013.01); *C12N 2720/12334* (2013.01); *C12N 2770/16034* (2013.01)

(58) Field of Classification Search
None
See application file for complete search history.

(56) References Cited

U.S. PATENT DOCUMENTS

| | | | |
|---|---|---|---|
| 4,547,367 | A | 10/1985 | Tabor et al. |
| 4,550,019 | A | 10/1985 | Polson |
| 4,916,213 | A | 4/1990 | Scannon et al. |
| 5,254,342 | A | 10/1993 | Shen et al. |
| 5,326,857 | A | 7/1994 | Yamamoto et al. |
| 5,338,689 | A | 8/1994 | Yves et al. |
| 5,367,054 | A | 11/1994 | Lee |
| 5,559,014 | A | 9/1996 | Estes et al. |
| 5,589,453 | A | 12/1996 | Greve |
| 5,643,579 | A | 7/1997 | Hung et al. |
| 5,665,534 | A | 9/1997 | Vandenbergh et al. |
| 5,750,394 | A | 5/1998 | Palese et al. |
| 5,783,193 | A | 7/1998 | Michael et al. |
| 5,786,340 | A | 7/1998 | Henning et al. |
| 5,789,230 | A | 8/1998 | Cotton et al. |
| 5,861,241 | A | 1/1999 | Hermann et al. |
| 6,045,854 | A | 4/2000 | Prieto et al. |
| 6,130,205 | A | 10/2000 | Stapleton et al. |
| 6,140,043 | A | 10/2000 | Dierich et al. |
| 6,156,883 | A | 12/2000 | Estes et al. |

(Continued)

FOREIGN PATENT DOCUMENTS

| | | |
|---|---|---|
| AU | 2003273206 | 12/2009 |
| AU | 2009238339 | 6/2011 |
| CA | 2487846 | 12/2003 |
| CN | 1330080 | 1/2002 |
| EP | 1532279 | 5/2005 |
| JP | 2012-515109 | 11/2012 |
| WO | WO 03/003985 | 1/2003 |

(Continued)

OTHER PUBLICATIONS

Glass et al., Review Article: Current Concepts Norovirus Gastroenteritis, 2009, The New England Journal of Medicine, vol. 361, No. 18, pp. 1776-1785.*

(Continued)

*Primary Examiner* — Benjamin P Blumel
(74) *Attorney, Agent, or Firm* — Frost Brown Todd LLC

(57) ABSTRACT

A substituted Norovirus capsid protein monomer, having only the P-domain, includes a foreign antigen inserted into one or more of three surface loops present on each P-domain monomer by molecular cloning. The antigen-P-domain monomer can assemble spontaneously into an octahedral, antigen-Norovirus P-particle, composed of 24 copies of the monomer. Each substituted P-domain monomer can contain one to three copies of the foreign antigen, for a total of 24-72 antigen copies on each antigen-P-particle. The antigen-P-particle is useful in methods for diagnosing, immunizing and treating individuals infected with a foreign virus and as a carrier for development of vaccines against many infectious and non-infectious diseases. The substituted monomer can be readily produced in *E. coli* and yeast, are highly stable and tolerate a wide range of physio-chemical conditions. The P-particle-VP8 chimeras may also serve as a dual vaccine, for example, against both rotavirus and norovirus.

2 Claims, 17 Drawing Sheets

(56) References Cited

U.S. PATENT DOCUMENTS

| | | | |
|---|---|---|---|
| 6,187,762 | B1 | 2/2001 | Mandeville, III et al. |
| 6,254,867 | B1 | 7/2001 | Reiser et al. |
| 6,258,789 | B1 | 7/2001 | German et al. |
| 6,300,090 | B1 | 10/2001 | Steinman et al. |
| 6,475,489 | B1 | 11/2002 | Rutter et al. |
| 6,572,862 | B1 | 6/2003 | Estes et al. |
| 6,593,080 | B1 | 7/2003 | Smith |
| 6,942,865 | B2 | 9/2005 | Estes et al. |
| 6,946,266 | B2 | 9/2005 | Neiman |
| 7,912,484 | B2 | 3/2011 | Sohn et al. |
| 7,977,098 | B2 | 7/2011 | Jiang et al. |
| 8,026,221 | B2 | 9/2011 | Jiang et al. |
| 8,277,819 | B2 | 10/2012 | Jiang et al. |
| 8,475,789 | B2 | 7/2013 | Bisgaard-Frantzen et al. |
| 8,486,421 | B2 | 7/2013 | Jiang et al. |
| 2002/0019991 | A1 | 2/2002 | Prieto et al. |
| 2004/0185556 | A1 | 9/2004 | Reed |
| 2007/0231320 | A1 | 10/2007 | Cook et al. |
| 2007/0280949 | A1 | 12/2007 | Alfa |
| 2008/0085553 | A1 | 4/2008 | Reed et al. |
| 2009/0280139 | A1 | 11/2009 | Jiang et al. |
| 2011/0152263 | A1 | 6/2011 | Jiang et al. |
| 2012/0009211 | A1 | 1/2012 | Tschopp et al. |

FOREIGN PATENT DOCUMENTS

| | | |
|---|---|---|
| WO | WO 03/101176 | 12/2003 |
| WO | WO 2005/030806 | 4/2005 |
| WO | WO 2005/032457 | 4/2005 |
| WO | WO 2006/138514 | 12/2006 |
| WO | WO 2010/144602 | 12/2010 |

OTHER PUBLICATIONS

Centers for Disease Control and Prevention, Norovirus Illness: Key Facts, 2015, Accession online on Feb. 9, 2015 at <<http://www.cdc.gov/norovirus/about/treatment.html>>.*
Centers for Disease Control and Prevention, Rotavirus vaccination, Accession online on Feb. 9, 2015 at <<http://www.cdc.gov/vaccines/vpd-vac/rotavirus/default.htm>>.*
Second Chinese Office Action dated Apr. 28, 2014 for Application No. CN 201080035302.2.
Adler, et al., "High Affinity Binding of the *Entamoeba histolytica* Lectin to Polyvalent *N*-Acetylgalactosaminides", Mar. 10, 1995, The Journal of Biol. Chem., vol. 270, No. 10, pp. 5164-5171.
Akita, E.M., et al., "Immunoglobulins from Egg-Yolk: Isolation and Purification", 1992, Journal of Food Science, 57, 629-634.
Akita, E.M., et al., "Production and purification of Fab' fragments from chicken egg yolk immunoglobulin Y (IgY)", 1993, K. Immunol Methods, 162, 155-64.
Amaral, J.A., et al., "Antienteropathogenic *Escherichia coli* immunoglobulin Y isolated from eggs laid by immunized Leghorn chickens", 2002, Res Vet Sci, 72, 229-34.
Atmar, R., et al., "Diagnosis of Non-cultivatable Gastroenteritis Viruses, the Human Caliciveruses", Jan. 2001, Clinical Microbiology Reviews, vol. 14, No. 1, pp. 15-37.
Bertolotti-Ciarlet, et al., "Structural Requirements for the Assembly of Norwalk Virus-Like particles", J. Virol, Apr. 2002, vol. 76, No. 8, pp. 4044-4055.
Brinker, J.P., et al., "Immunoglobulin M Antibody Test to Detect Genogroup II Norwalk-Like Virus Infection", Sep. 1999, Journal for Clinical Microbiology, vol. 37, No. 9, 2983-2986.
Bruss, V., et al., "Mutational Analysis of Hepatitis B Surface Antigen Particle Assembly and Secretion", J. Virol, Jul. 1991, vol. 65, No. 7, pp. 3813-3820.
Bu, W., et al., "Structural Basis for the receptor Binding Specificity of Norwalk Virus", J. Virol, Jun. 2008, vol. 82, No. 11, pp. 5340-5347.
Burton-MacLeod, J.A., et al. "Evaluation and Comparison of Two Commercial Enzyme-Linked Immunosorbent Assay Kits for Detection of Antigenically Diverse Human Noroviruses in Stool Samples", Jun. 2004, Journal of Clinical Microbiology, vol. 42, No. 6, pp. 2587-2595.
Cao, S., et al., "Structural Basis for the Recognition of Blood Group Triaccharides by Norovirus", J. Virol, Jun. 2007, vol. 81, No. 11, pp. 5949-5957.
Chatterji, et al., "Chemical conjugation of heterologous proteins on the surface of Cowpea mosaic virus", Bioconjug Chem, 2004, 15:807-13.
Chatterji, A., et al., "Cowpea Mosaic Virus: From the Presentation of Antigenic Peptides to the Display of Active Biomaterials", Intervirology, 2002, 45 (4-6), pp. 362-370.
Chen, et al., "Inter-and Intragenus Structural Variation in Caliciviruses and Their Functional Implications", J. Virol, Jun. 2004, vol. 78, No. 12, pp. 6469-6479.
Chen, et al., "Packaging of gold particles in viral capsids", J Nacosci Nanotechnol, 2005, 5:2029-33.
Chen, C., et al., "Nanoparticle-templated assembly of viral protein Cages", Nano Lett, 2006, 6:611-15.
Choi, A.H., et al., "Functional Mapping of Protective Domains and Epitopes in the Rotavirus VP6 Protein", J. Virol, Dec. 2000, vol. 74, No. 24, pp. 11574-11580.
Choi, A.H., et al., "Functional mapping of protective epitopes within the rotavirus VP6 protein in mice belonging to different haplotypes", Vaccine, Jan. 30, 2003, 21(7-8), pp. 761-767.
Cooper, H.M., et al., "Production of polyclonal antisera", 2009, Curr Protoc Neurosci, 2009, Chapter 5, Unit 5.5.
Crisci, et al., "Chimeric calicivitus-like particles elicit protective anti-viral cyotoxic responses without adjuvant", Virology, May 10, 2009, vol. 387, No. 2, pp. 303-312.
Dias da Silva, et al., "IgY: a promising antibody for use in immunodiagnostic and in immunotherapy", 2010, Vet Immunol Immunopathol, 135, 173-80.
Douglas, al., "Viruses: making friends with old foes", Science, 2006, 312:873-75.
Douglas T., "A bright bio-inspired future", Science, 2003, 299:1192-93.
Dragnea, et al., "Gold nanoparticles as spectroscopic enhancers for in vitro studies on single viruses", J Am Chem Soc, 2003, 125:6375-75.
Eldon Biologicals A/S, Eldoncar Home Kit 2511 Manufacture Catalog, published on website, searched on Sep. 2008, in corresponding U.S. Appl. No. 11/264,992.
Eldon Biologicals A/S, Eldoncar Home Kit 2511 Manufacture Protocol, published on website, searched on Sep. 2008, in corresponding U.S. Appl. No. 11/264,992.
EldonCard Home Blood Testing kit Published on Website, searched on Sep. 2008, in corresponding U.S. Appl. No. 11/264,992.
Erdman, D.D., et al., "Serum Immunoglobulin a Response to Norwalk Virus Infection", Jun. 1989, Journal of Clinical Microbiology, vol. 27, No. 6, pp. 1417-1418.
Estes, M., et al., "Norwalk Virus Vaccines: Challenges and Progress", 2000, The Journal of Infectious Diseases, vol. 181, Suppl. 2, pp. S367-S373.
Evaluation Report for Eldon Biologicals A/S, published 2004, in corresponding U.S. Appl. No. 11/264,992.
Farkas, T., et al., "Homologous versus Heterologous Immune Responses to Norwalk-Like Viruses among Crew Members after Acute Gastroenteritis Outbreaks on 2 Navy Vessels", Jan. 2003, The Journal of Infectious Diseases, vol. 187, pp. 187-193.
Farkas, T., et al., "Molecular Detection and Sequence Analysis of Human Caliciviruses From Acute Gastroenteritis Outbreaks in Hungary", Jan. 2002, Journal of Medical Virology, vol. 67, pp. 567-573.
Feng, X., et al., "Library screen inhibitors targeting norovirus binding to hosto-blood group antigen receptors", 2007, Antimicrob Agents Chemother, 51, 324-31.
Glass, R.I., et al., "Norovirus gastroenteritis", 2009, N Engl J Med, 361, 1776-85.
Gray, J.J., et al., "Prevalence of Antibodies to Norwalk Virus in England: Detection by Enzyme-Linked Immunosorbent Assay Using Baculovirus-Expressed Norwalk Virus Capsid Antigen", Apr. 1993, Journal of Clinical Microbiology, vol. 31, No. 4, pp. 1022-1025.
Green, J., et al., "Capsid protein diversity among the Norwalk-like viruses", 2000, Virus Genes, 20:227-36. (Abstract).
Green, K.Y., et al., "Taxonomy of the Caliciviruses", 2000, The Journal of Infectious Diseases, vol. 181 (Suppl 2), pp. S322-S330.

(56) References Cited

OTHER PUBLICATIONS

Grgacic, et al., "Virus-like particles: passport to immune recognition", Methods Sep. 2006, vol. 40, No. 1, pp. 60-65.
Guix, et al., 2007, J. Virol., vol. 81, No. 22, pp. 12238-12248.
Hale, A.D., et al., "Expression and Self-Assembly of Grimsby Virus: Antigenic Distinction from Norwalk and Mexico Viruses", Jan. 1999, Clinical and Diagnostic Laboratory immunology, vol. 6, No. 1, pp. 142-145.
Hale, A.D., et al., "Identification of an Epitope Common to Genogroup 1 'Norwalk-Like Viruses'", Apr. 2000, Journal of Clinical Microbiology, vol. 38, No. 4, pp. 1656-1660.
Hardy, M.E., et al., "Specific Proteolytic Cleavage of Recombinant Norwalk Virus Capsid Protein", J. Viol, Mar. 1995, vol. 69, No. 3, pp. 1693-1698.
Harrington, P., et al., "Binding Norwalk Virus-Like Particles to ABH Histo-Blood Group Antigens is Blocked by Antisera from Infected Human Volunteers or Experimentally Vaccinated Mice", Dec. 2002, Journal of Virology, vol. 76, No. 23., pp. 12335-12343.
Harrington, P., et al., "Norovirus Capture with Histo-Blood Group Antigens Reveals Novel Virus-Ligand Interactions", Mar. 2004, Journal of Virology, vol. 78, No. 6, pp. 2035-3045.
Hennessy, E.P., et al., "Norwalk Virus Infection and Disease is Associated with ABO Histo-Blood Group Type", 2003, The Journal of Infectious Diseases, vol. 188, pp. 176-177.
Hoffman, R., ed., *Hematology Basic Principles and Practice*, 2$^{nd}$ Ed., 1995, Churchill Livingston NY, NY.
http://acronyms.thefreedictionary.com/kit, cited as searched on Feb. 18, 2008 by Examiner in corresponding U.S. Appl. No. 11/264,992, printed on Feb. 22, 2008, p. 1-4.
http://encycolpedia.thefreedictionary.com/assay, cited as searched on Feb. 18, 2008 by Examiner in corresponding U.S. Appl. No. 11/264,992, printed on Feb. 22, 2008, p. 1-5.
Huang, P., et al., "Norovirus and Histo-Blood Group Antigens: Demonstration of a Wide Spectrum of Strain Specificities and Classification of Two Major Binding Groups among Multiple Binding Patterns", Jun. 2005, Journal of Virology, vol. 79, No. 11, pp. 6714-6722.
Huang, P., et al., "Noroviruses Bind to Human ABO, Lewis, and Secretor Histo-Blood group Antigens: Identification of 4 Distinct Strain-Specific Patterns", Jul. 1, 2003, The Journal of Infectious Disease, vol. 188, No. 19, pp. 19-31.
Hutson, A., et al., "Norwalk Virus-Like Particle Hemagglutination by Binding to H Histo-Blood Group Antigens", Jan. 2003, Journal of Virology, vol. 77, No. 1, pp. 405-415.
Hutson, A.M., et al. "ABO Phenotype Associated with Norwalk Virus Infection and Disease may be Related to Norwalk Virus-Like particle Binding H Antigens", Apr. 2002), Gastroenterology, vol. 122, No. 4, Suppl. 1, pp. A-141. XP009054158 & Digestive Disease Week and the 103$^{rd}$ Annual Meeting of the American Gastroenterological Association; San Francisco, CA, USA; May 19-22, 2002.
Hutson, A.M., et al., "Norwalk Virus Infection and Disease is Associated with ABO Histo-Blood Group Type", 2002, The Journal of Infectious Diseases, 185, pp. 1335-1337.
Immuncor Inc., Manufacture Advertisement, published on Immucor Website, searched Sep. 2008, in corresponding U.S. Appl. No. 11/264,992.
Jennings, et al., "The coming of age of virus-like particle vaccines", Biological Chemistry, May 1, 2008, vol. 389, No. 5, pp. 521-536.
Jiang, X., et al., "Baculovirus expression and antigenic characterization of the capsid proteins of three Norwalk-like viruses", 2002, Archives of Virology, vol. 147, pp. 119-130.
Jiang, X., et al., "Expression, Self-Assembly, and Antigenicity of the Norwalk virus capsid protein", 1992, Journal of Virology, 66:6527-32.
Jiang, X., et al., "Expression, Self-Assembly, and Antigenicity of a Snow Mountain Agent-Like Calicivirus Capsid Protein", Jun. 1995, Journal of Clinical Microbiology, vol. 33, No. 6, pp. 1452-1455.
Jiang, X., et al., "Human Milk Contains Elements that Block Binding of Noroviruses to Human Histo-Blood Antigens in Saliva", Nov. 15, 2004, The Journal of Infectious Diseases, vol. 190, pp. 1850-1859.
Jiang, X., et al., "Norwalk Virus Genome Cloning and Characterization", Dec. 14, 1990, Science, vol. 250, pp. 1580-1583.
Jiang, X., et al., "Sequence and Genomic Organization of Norwalk Virus", 1993, Virology, 195, pp. 51-61.
Kumar, S., et al., "MEGA2: molecular evolutionary genetics analysis software", 2001, Bioinformatics Applications Note, vol. 17, No. 12, pp. 1244-1245.
Kurdyashov, et al., "Characterization of a mouse monoclonal IgG3 antibody to the tumor-associated globo H structure produced by Immunization with a synthetic glycoconjugate", 1998, Glycoconjugate Journal, vol. 15, pp. 243-249.
Lew, J.F., et al., "Molecular Characterization of Hawaii Virus and Other Norwalk-like Viruses: Evidence for Genetic Polymorphism among Human Caliciviruses", Mar. 1994, The Journal of Infectious Diseases, vol. 170, pp. 535-542.
Lindesmith, L., et al., "Human Susceptibility and Resistance to Norwalk Virus Infection", May 2003, Natural Medicine, vol. 9, No. 5, p. 548-553.
Liou, J.F., et al. "Passive protection effect of chicken egg yolk immunoglobulins on enterovirus 71 infected mice", 2010, Vaccine, 28, 8189-96.
Manayani, D.J., "A Viral Nanoparticle with Dual Function as an Anthrax Antitoxin and Vaccine", PLoS Pathog., Oct. 5, 2007, vol. 3, No. 10, pp. 1422-1431.
Marionneau, S., et al., "ABH and Lewis Histo-Blood Group Antigens, A Model for the Meaning of Oligosaccharide Diversity in the Face of a Changing World", Jul. 2001, Biochimie, 83(7):565-73.
Marionneau, S., et al., "Norwalk Virus Binds to Histo-Blood Group Antigens Present on Gastroduodenal Epithelial Cells of Secretor Individuals", Jun. 2002, Gastroenterology, 122, pp. 1697-1677.
McNeal, M.M., et al., "Antibody-Dependant and Independent Protection following Intranasal Immunization of Mice with Rotavirus Particles", J. Virol, Sep. 1999, vol. 73, No. 9, pp. 7565-7573.
Merriam-Webster's Collegiate Dictionary, Tenth Edition copyright 1998 by Merriam-Webster, Inc., p. 924.
Nguyen, H.H., et al., "Prophylactic and therapeutic efficacy of avian antibodies against influenza virus H5N1 and H1N1 in mice", 2010, PLoS One, 5, e10152.
Nicolas, K.B., et al., "GeneDoc: Analysis and Visualization of Genetic Variation", http://www.psc.edu/biomed/genedoc/ebinet.htm, pp. 1-5.
Nurminen, K., et al., "Prevalence of norovirus GII-4 antibodies in Finnish children", 2011, J Med Virol, 83, 525-31.
Ochoa, et al., "Generation and structural analysis of reactive empty particles derived from an icosahedral virus", Chem Biol, 2006, 13:771-78.
Oriol, R., et al., "Insights into the Expression of ABH and Lewis Antigens through Human Bone Marrow Transplantation", 1981, Am Journal Hum Genet, vol. 33, pp. 551-560.
Patel, M.M., et al., "Systematic literature review of role of noroviruses in sporadic gastroenteritis", 2008, Emerg Infect Dis, 14, 1224-31.
Peabody, D.S., "A Viral Platform for Chemical Modification and Multivalent Display", J Nanobiotechnology, 2003, 1:5.
Pelosi, E., et al., "The Seroepidemiology of Genogroup 1 and Genogroup 2 Norwalk-Like Viruses in Italy", Apr. 1, 1999, Journal of Medical Virology, vol. 58, issue 1, pp. 93-99.
Prasad, B.V., et al., "X-Ray Crystallographic Structure of the Norwalk Virus Capsid", Oct. 8, 1999, Science, vol. 286, pp. 287-290.
Radloff, et al., "Metal nanoshell assembly on a virus bioscaffold", Nano Lett, 2005, 5:1187-91.
Reeck, A., et al., "Serological correlate of protection against norovirus-induced gastroenteritis", 2010, J Infect Dis, 202, 1212-8.
Schwartz, S., et al., "Norovirus gastroenteritis causes severe and lethal complications after chemotherapy and hematopoietic stem cell transplantation", 2011, Blood, 117, 5850-6.
Silverman, *The Organic Chemistry of Drug Design and Drug Action*, 1992, Academic Press, pp. 4-47.
Sixth International Symposium on Positive Strand RNA Viruses (May 28-Jun. 2, 2001). Institut Pasteur, Paris, France; Scientific Program Abstracts "Norwalk Virus Binds to H Type 1 Histo-Blood Group Antigen Present on Gastro-Duodenal Epithelial Cells of 'Secretor' Phenotype Individuals".

(56) References Cited

OTHER PUBLICATIONS

Tamura, M., et al., "Interaction of Recombinant Norwalk Virus Particles with the 105-Kilodalton Cellular Binding Protein, a Candidate Receptor molecule for Virus Attachment", Dec. 2000, Journal of Virology, vol. 74, No. 24, pp. 11589-11597.
Tan, M., et al. "Elucidation of strain-specific interaction of a GII-4 norovirus with HBGA receptors by site-directed mutagenesis study", Virology, Sep. 30, 2008, vol. 379, No. 2, pp. 324-334.
Tan, M., et al., "C-terminal Arginine Cluster is Essential for Receptor Binding of Norovirus Capsid Protein", J. Virol. Aug. 2006, vol. 80, No. 15, pp. 7322-7331.
Tan, M., et al., "*E. coli*-Expressed Recombinant Norovirus Capsid Proteins Maintain Authentic Antigenicity and Receptor Binding Capability", 2004, Journal of Medical Virology, vol. 74, pp. 641-649.
Tan, M., et al., "Mutations within the P2 Domain of Norovirus Capsid Affect Binding to Human Histo-Blood Group Antigens: Evidence for a Binding Pocket", Dec. 2003, Journal of Virology, vol. 77, No. 23, pp. 12562-12571.
Tan, M., et al., "Noroviral P particles: Structure, function and applications in virus-host interaction", Virology, Dec. 5, 2008, vol. 382, No. 1, pp. 115-123.
Tan, M., et al., "Norovirus P particle, a novel platform for vaccine development and antibody production", 2011, J Virol, 85, 753-64.
Tan, M., et al., "Norovirus P particle: a subviral nanoparticle for vaccine development against norovirus, rotavirus and influenza virus" Nanomedicine, Jun. 2012, 7(6):889-897.
Tan, M., et al., "Norovirus and its histo-blood group antigen receptors: an answer to a historical puzzle", Jun. 6, 2005, Trends in Microbiology, vol. 13, No. 6, pp. 285-293.
Tan, M., et al., "Norovirus Gastroenteritis, Carbohydrate Receptors, and Animal Models", 2010, PLoS Pathog, 6:8, e100983.
Tan, M., et al. "Terminal modifications of norovirus P domain resulted in a new type of subviral particles, the small P particles", 2011, Virology, 410, 345-52.
Tan, M., et al., "The P Domain of Norovirus Capsid Protein Forms a Subviral Particle That Binds to Histo-Blood Group Antigen Receptors", Nov. 2005, Journal of Virology, vol. 79, No. 22, pp. 14017-14030.
Tan, M., et al., "The P Domain of Norovirus Capsid Protein Forms Dimer and Binds to Histo-Blood Group Antigen Receptors", Jun. 2004, Journal of Virology, vol. 78, No. 12, pp. 6233-6242.
Treanor, J.J. et al., "Development of an Enzyme Immunoassay for the Hawaii Agent of Viral Gastroenteritis", Dec. 1988, Journal of Virol Methods, 22(2-3):207-14.
Vega, C., et al., "Egg yolk IgY: protection against rotavirus induced diarrhea and modulatory effect on the systemic and mucosal antibody responses in newborn calves", 2011, Vet Immunol Immunopathol, 142, 156-69.
Wang, L., et al., "Polyvalent complexes for vaccine development", Biomaterials, 2013, 34, pp. 4480-4492.
White, L.J., et al., "Attachment and Entry of Recombinant Norwalk Virus Capsids to Cultured Human and Animal Cell Lines", Oct. 1996, Journal of Virology, vol. 70, No. 10, pp. 6589-6597.
Wobus, C.E., et al., "Replication of Norovirus in Cell Culture Reveals a Tropism for Dendritic Cells and Macrophages", Dec. 2004, PLoS Biology, vol. 2, Issue 12, pp. 0001-0009.
WordReference.com, English Dictionary, search for word "affixed", searched on Jan. 16, 2010, in corresponding U.S. Appl. No. 11/264,992.
Xia, M., et al., "A candidate dual vaccine against influenza and noroviruses", Vaccine, Oct. 13, 2011, 29(44): 7670-7677.
Xia, M., et al., "Norovirus Capsid Protein Expressed in Yeast Forms Virus-like Particles and Stimulates Systemic and Mucosal Immunity in Mice Following an Oral Administration of Raw Yeast Extracts", J Med Virol, Jan. 2007, vol. 79, No. 1, pp. 74-83.
Xu, Y., et al., "Application of chicken egg yolk immunoglobulins in the control of terrestrial and aquatic animal diseases: A review", 2011, Biotechnol Adv., 29:860-868.
Yang, Y., et al., *capsid protein, partial*, GenBank: ADF50093.1, submitted Feb. 24, 2010.
Australian Information Statement Documentary Search Results dated May 16, 2007 for Application No. AU 2003273206.
Canadian Office Action dated Jan. 26, 2010 for Application No. CA 2,487,846.
Canadian Response and Amendment filed Jul. 16, 2010 for Application No. CA 2,487,846.
Canadian Response and Amendment filed Mar. 3, 2011 for Application No. CA 2,487,846.
Chinese Office Action dated Jul. 11, 2013 for Application No. CN 201080035302.2.
International Search Report dated Jan. 14, 2005 for Application No. PCT/US03/17247.
International Preliminary Examination Report dated Mar. 21, 2005 for Application No. PCT/US03/17247.
International Search Report and Written Opinion dated Mar. 31, 2011 for Application No. PCT/US2010/038008.
International Preliminary Report on Patentability and Written Opinion dated Dec. 22, 2011 for Application No. PCT/US2010/038008.
International Search Report and Written Opinion dated Oct. 16, 2013 for Application No. PCT/US2013/050004.
Supplementary European Search Report dated Jan. 7, 2013 for Application No. EP 10786797.0.
Supplementary Partial European Search Report dated Sep. 20, 2005 for Application No. EP 03 74 1844.
Abstract and English Machine Translation of Chinese Patent No. CN 1330080A.
Abstract and English Machine Translation of Japanese Patent No. JP 2012-515109.
U.S. Appl. No. 12/040,530, filed Feb. 29, 2008.
U.S. Appl. No. 10/520,087, filed Jun. 2, 2003.
U.S. Appl. No. 60/385,283, filed May 31, 2002.
U.S. Appl. No. 60/385,296, filed May 31, 2002.
U.S. Appl. No. 61/185,564, filed Jun. 9, 2009.
U.S. Appl. No. 61/224,696, filed Jul. 10, 2009.
U.S. Appl. No. 61/670,288, filed Jul. 11, 2012.

\* cited by examiner

SEQUENCE LISTING

<160> NUMBER OF SEQ ID NOS: 12

<210> SEQ ID NO 1
<211> LENGTH: 5
<212> TYPE: PRT
<213> ORGANISM: Norovirus

<400> SEQUENCE: 1

Ile Ala Gly Ser His
1               5

<210> SEQ ID NO 2
<211> LENGTH: 4
<212> TYPE: PRT
<213> ORGANISM: Norovirus

<400> SEQUENCE: 2

Thr Asn Asn Asp
1

```
<210> SEQ ID NO 3
<211> LENGTH: 4
<212> TYPE: PRT
<213> ORGANISM: Norovirus

<400> SEQUENCE: 3

Asp Gly Asn Asn
1

<210> SEQ ID NO 4
<211> LENGTH: 5
<212> TYPE: PRT
<213> ORGANISM: Artificial Sequence
<220> FEATURE:
<223> OTHER INFORMATION: a short peptide sequence that can easily be
      manufactured artificially

<400> SEQUENCE: 4

Cys Asn Gly Arg Cys
1               5

<210> SEQ ID NO 5
<211> LENGTH: 9
<212> TYPE: PRT
<213> ORGANISM: Artificial Sequence
<220> FEATURE:
<223> OTHER INFORMATION: a short peptide sequence that can easily be
      manufactured artificially

<400> SEQUENCE: 5

Cys Asp Cys Arg Gly Asp Cys Phe Cys
1               5

<210> SEQ ID NO 6
<211> LENGTH: 8
<212> TYPE: PRT
<213> ORGANISM: Artificial Sequence
<220> FEATURE:
<223> OTHER INFORMATION: a small peptide tag that can easily be
      manufactured artificially

<400> SEQUENCE: 6

Asp Tyr Lys Asp Asp Asp Asp Lys
1               5

<210> SEQ ID NO 7
<211> LENGTH: 10
<212> TYPE: PRT
<213> ORGANISM: Artificial Sequence
<220> FEATURE:
<223> OTHER INFORMATION: a small peptide tag that can easily be
      manufactured artificially

<400> SEQUENCE: 7

Glu Gln Lys Leu Ile Ser Glu Glu Asp Leu
1               5                   10

<210> SEQ ID NO 8
<211> LENGTH: 106
<212> TYPE: DNA
<213> ORGANISM: Artificial Sequence
<220> FEATURE:
<223> OTHER INFORMATION: a short primer sequence that can easily be
      manufactured artificially
```

```
<400> SEQUENCE: 8
caccactgac acaaaccacc accaccatca tcaccacgat cttcaaactg gccggccagt    60
ttgaagatcg tggtgatgat ggtggtggtg gtttgtgtca gtggtg                 106

<210> SEQ ID NO 9
<211> LENGTH: 90
<212> TYPE: DNA
<213> ORGANISM: Artificial Sequence
<220> FEATURE:
<223> OTHER INFORMATION: short primer sequence that is easy to
      manufacture artificially

<400> SEQUENCE: 9
gttcaataca ccactagtac aaacatcgat atccttcaaa ctggcgccag tttgaaggat    60
atcgatgttt gtactagtgg tgtattgaac                                    90

<210> SEQ ID NO 10
<211> LENGTH: 100
<212> TYPE: DNA
<213> ORGANISM: Artificial Sequence
<220> FEATURE:
<223> OTHER INFORMATION: short primer sequence that is easy to
      manufacture artificially

<400> SEQUENCE: 10
tacaccactg acavaaactc tagacacaga tctaatgatc ttcaaactgg ccagtttgaa    60
gatcattaga tctgtgtcta gagtttgtgt cagtggtgta                        100

<210> SEQ ID NO 11
<211> LENGTH: 539
<212> TYPE: PRT
<213> ORGANISM: Norovirus strain VA387

<400> SEQUENCE: 11
```

Met Lys Met Ala Ser Asn Asp Ala Ser Pro Ser Asp Gly Ser Thr Ala
1               5                   10                  15

Asn Leu Val Pro Glu Val Asn Asn Glu Val Met Ala Leu Glu Pro Val
            20                  25                  30

Val Gly Ala Ala Ile Ala Ala Pro Val Ala Gly Gln Gln Asn Val Ile
        35                  40                  45

Asp Pro Trp Ile Arg Asn Asn Phe Val Gln Ala Pro Gly Gly Glu Phe
    50                  55                  60

Thr Val Ser Pro Arg Asn Ala Pro Gly Glu Ile Leu Trp Ser Ala Pro
65                  70                  75                  80

Leu Gly Pro Asp Leu Asn Pro Tyr Leu Ser His Leu Ala Arg Met Tyr
                85                  90                  95

Asn Gly Tyr Ala Gly Gly Phe Glu Val Gln Val Ile Leu Ala Gly Asn
            100                 105                 110

Ala Phe Thr Ala Gly Lys Val Ile Phe Ala Ala Val Pro Pro Asn Phe
        115                 120                 125

Pro Thr Glu Gly Leu Ser Pro Ser Gln Val Thr Met Phe Pro His Ile
    130                 135                 140

Ile Val Asp Val Arg Gln Leu Glu Pro Val Leu Ile Pro Leu Pro Asp
145                 150                 155                 160

Val Arg Asn Asn Phe Tyr His Tyr Asn Gln Ser Asn Asp Ser Thr Ile
                165                 170                 175

Lys Leu Ile Ala Met Leu Tyr Thr Pro Leu Arg Ala Asn Asn Ala Gly
            180                 185                 190

```
Asp Asp Val Phe Thr Val Ser Cys Arg Val Leu Thr Arg Pro Ser Pro
            195                 200                 205
Asp Phe Asp Phe Ile Phe Leu Val Pro Pro Thr Val Glu Ser Arg Thr
        210                 215                 220
Lys Pro Phe Thr Val Pro Ile Leu Thr Val Glu Glu Met Ser Asn Ser
225                 230                 235                 240
Arg Phe Pro Ile Pro Leu Glu Lys Leu Tyr Thr Gly Pro Ser Ser Ala
                245                 250                 255
Phe Val Val Gln Pro Gln Asn Gly Arg Cys Thr Thr Asp Gly Val Leu
            260                 265                 270
Leu Gly Thr Thr Gln Leu Ser Ala Val Asn Ile Cys Thr Phe Arg Gly
        275                 280                 285
Asp Val Thr His Ile Ala Gly Ser His Asp Tyr Ile Met Asn Leu Ala
    290                 295                 300
Ser Gln Asn Trp Asn Asn Tyr Asp Pro Thr Glu Ile Pro Ala Pro
305                 310                 315                 320
Leu Gly Thr Pro Asp Phe Val Gly Lys Ile Gln Gly Met Leu Thr Gln
                325                 330                 335
Thr Thr Arg Glu Asp Gly Ser Thr Arg Ala His Lys Ala Thr Val Ser
            340                 345                 350
Thr Gly Thr Val His Phe Thr Pro Lys Leu Gly Ser Val Gln Tyr Thr
        355                 360                 365
Thr Asp Thr Asn Asn Asp Phe Gln Thr Gly Gln Asn Thr Lys Phe Thr
    370                 375                 380
Pro Val Gly Val Ile Gln Asp Gly Asn Asn His Gln Asn Glu Pro Gln
385                 390                 395                 400
Gln Trp Val Leu Pro Asn Tyr Ser Gly Arg Thr Gly His Asn Val His
                405                 410                 415
Leu Ala Pro Ala Val Ala Pro Thr Phe Pro Gly Glu Gln Leu Leu Phe
            420                 425                 430
Phe Arg Ser Thr Met Pro Gly Cys Ser Gly Tyr Pro Asn Met Asn Leu
        435                 440                 445
Asp Cys Leu Leu Pro Gln Glu Trp Val Gln His Phe Tyr Gln Glu Ala
    450                 455                 460
Ala Pro Ala Gln Ser Asp Val Ala Leu Leu Arg Phe Val Asn Pro Asp
465                 470                 475                 480
Thr Gly Arg Val Leu Phe Glu Cys Lys Leu His Lys Ser Gly Tyr Val
                485                 490                 495
Thr Val Ala His Thr Gly Pro His Asp Leu Val Ile Pro Pro Asn Gly
            500                 505                 510
Tyr Phe Arg Phe Asp Ser Trp Val Asn Gln Phe Tyr Thr Leu Ala Pro
        515                 520                 525
Met Gly Asn Gly Ala Gly Arg Arg Ala Leu
    530                 535

<210> SEQ ID NO 12
<211> LENGTH: 318
<212> TYPE: PRT
<213> ORGANISM: Norovirus strain VA387

<400> SEQUENCE: 12

Ser Arg Thr Lys Pro Phe Thr Val Pro Ile Leu Thr Val Glu Glu Met
1               5                   10                  15
Ser Asn Ser Arg Phe Pro Ile Pro Leu Glu Lys Leu Tyr Thr Gly Pro
            20                  25                  30
```

```
Ser Ser Ala Phe Val Val Gln Pro Gln Asn Gly Arg Cys Thr Thr Asp
    35                  40                  45

Gly Val Leu Leu Gly Thr Thr Gln Leu Ser Ala Val Asn Ile Cys Thr
    50                  55                  60

Phe Arg Gly Asp Val Thr His Ile Ala Gly Ser His Asp Tyr Ile Met
65                  70                  75                  80

Asn Leu Ala Ser Gln Asn Trp Asn Asn Tyr Asp Pro Thr Glu Glu Ile
            85                  90                  95

Pro Ala Pro Leu Gly Thr Pro Asp Phe Val Gly Lys Ile Gln Gly Met
            100                 105                 110

Leu Thr Gln Thr Thr Arg Glu Asp Gly Ser Thr Arg Ala His Lys Ala
        115                 120                 125

Thr Val Ser Thr Gly Thr Val His Phe Thr Pro Lys Leu Gly Ser Val
        130                 135                 140

Gln Tyr Thr Thr Asp Thr Asn Asn Asp Phe Gln Thr Gly Gln Asn Thr
145                 150                 155                 160

Lys Phe Thr Pro Val Gly Val Ile Gln Asp Gly Asn Asn His Gln Asn
            165                 170                 175

Glu Pro Gln Gln Trp Val Leu Pro Asn Tyr Ser Gly Arg Thr Gly His
            180                 185                 190

Asn Val His Leu Ala Pro Ala Val Ala Pro Thr Phe Pro Gly Glu Gln
        195                 200                 205

Leu Leu Phe Phe Arg Ser Thr Met Pro Gly Cys Ser Gly Tyr Pro Asn
        210                 215                 220

Met Asn Leu Asp Cys Leu Leu Pro Gln Glu Trp Val Gln His Phe Tyr
225                 230                 235                 240

Gln Glu Ala Ala Pro Ala Gln Ser Asp Val Ala Leu Leu Arg Phe Val
            245                 250                 255

Asn Pro Asp Thr Gly Arg Val Leu Phe Glu Cys Lys Leu His Lys Ser
            260                 265                 270

Gly Tyr Val Thr Val Ala His Thr Gly Pro His Asp Leu Val Ile Pro
        275                 280                 285

Pro Asn Gly Tyr Phe Arg Phe Asp Ser Trp Val Asn Gln Phe Tyr Thr
    290                 295                 300

Leu Ala Pro Met Gly Asn Gly Ala Gly Arg Arg Arg Ala Leu
305                 310                 315
```

ANTIGEN-NOROVIRUS P-DOMAIN MONOMERS AND DIMERS, ANTIGEN NOROVIRUS P-PARTICLE MOLECULES, AND METHODS FOR THEIR MAKING AND USE

CROSS-REFERENCE TO RELATED APPLICATIONS

This application is a continuation application of U.S. application Ser. No. 12/797,396, filed Jun. 9, 2010 (pending), which claims priority to U.S. Provisional Application 61/185,564, filed Jun. 9, 2009, and to U.S. Provisional Application 61/224,696, filed Jul. 10, 2009, the disclosures of which are incorporated herein by reference in their entireties.

INTEREST

This invention was made with government support under AI037093 and AI055649 awarded by the National Institutes of Health and under W81XWH-04-10066 awarded by the United States Army Medical Research and Material Command. The Government has certain rights in the invention.

FIELD OF THE INVENTION

The present invention relates in general to the P-domain of the Norovirus (NOR) capsid protein and NOR P-particles, the making of antigen-Norovirus P-domain monomers, antigen-Norovirus P-domain dimers and antigen-Norovirus P-particle molecules, and their use for antiviral drugs, drug delivery systems, and vaccine development.

BACKGROUND OF THE INVENTION

Biomaterials and bioengineering are fast growing areas that have become critical parts of modern medicine. Because of their versatility and propensity to form arrays, viral protein cages are ideal substrates to build presentation systems. Through genetic engineering, the self-assembled viral structural protein is an outstanding platform for biomaterial synthesis and a scaffold for integration of foreign molecules in designed patterns, which can be used as vaccines or drugs.

A recent example using viral particles for antigen presentation is the chimera of flock house virus (FHV) VLP with a 180-amino acid antigen insertion of *Bacillus anthracis*, described by Manayani et al. The recombinant virus-like particles function both as an anthrax antitoxin and as a molecular scaffold for an anthrax vaccine, and combine the functions of an anthrax antitoxin and vaccine in a single compound. Another example is the Cowpea mosaic virus (CPMV), described by Chatterji et al., which includes the use of Cowpea mosaic virus for both epitope presentation and as a matrix for the attachment of peptides and proteins. Entire proteins have been chemically cross-linked to lysine and cysteine residues genetically engineered on the coat protein of icosahedral CPMV particles. Also, a hepatitis B virus (HBV) capsid-like particle (CLP) containing a surface antigen (OspA) of *Borrelia burgdorferi* has been described.

Norovirus (NOR), also known previously as "Norwalk-Like Virus" (NLV) or small round structured virus, is the most important viral pathogen of epidemic acute gastroenteritis that occurs in both developed and developing countries. These genetically diverse viruses comprise two major genogroups (GI and GII) and approximately 30 genotypes. NORs belong to the Caliciviridae family and are icosahedral, single stranded, positive-sense RNA viruses whose capsids are composed of 180 copies of a single major structural protein.

In the past, the biological characterization of human NORs had been hampered because the virus failed to grow in cell cultures efficiently and no suitable animal models had been established for virus replication. Human stool samples obtained from outbreaks and from human volunteer studies were the only source of the virus, yet the concentration of the virus in stool is so low that virus detection with routine electron microscopy was not possible. However, the recently successful expression of NOR capsid proteins by baculoviruses (double stranded DNA viruses which infect mainly insects) in insect cells has provided a valuable alternative for studying the immunology, epidemiology and pathogenesis of NORs. The viral capsid protein monomers produced self-assemble into virus-like particles (VLPs). These VLPs are morphologically and antigenically indistinguishable from authentic viruses found in human feces, providing a useful tool for the development of immunological assays and the study of receptor-virus interaction.

The atomic structure of the recombinant NOR capsid protein indicates that it contains 180 capsid protein monomers organized into 90 dimeric capsomers that form a T=3 icosahedron. Data from cryoelectron microscopy and X-ray crystallography showed that the viral capsid protein folds into two major domains, the N-terminal Shell (S) domain and the C-terminal Protrusion (P) domain. The S-domain forms the interior shell, while the P-domain builds up arch-like structures that extend from or protrude from the shell. Morphogenesis studies showed that the S-domain contains elements required for assembly of the interior shell of the capsid, whereas intermolecular contacts between dimeric subunits of the P-domain increase the stability of the capsid. These two domains are linked through a 8-10-residue (amino acid) hinge. The P-domain is further divided into P1 and P2 domains, with the latter located at the most exterior surface of the capsid. In contrast to the S and P1 domains, the P2-domain has a high sequence variation. Since the P-domain is located at the most exterior surface of the viral particle and contains the most variable sequence, it is believed that the P-domain is responsible for host interactions, immune recognition, receptor binding and immune responses. It has been shown that isolated P-domains having a hinge (but lacking the S-domain) form dimers in vitro that maintain binding to human histo-blood group antigen (HBGA) receptors.

HBGAs are a heterogeneous group of complex glycans and related carbohydrates. NORs recognize human HBGAs as receptors in a diverse, strain-specific manner. Among the HBGAs, the most commonly encountered blood groups are ABO (ABH) and Lewis. The biosynthetic pathways used in forming antigens in the ABH and Lewis blood group systems are interrelated.

Human HBGAs are present on many cell types including red blood cells and vascular endothelial cells, as well as on the mucosal epithelia of the gastrointestinal, uro-genital and respiratory tracts. They can also be present in a soluble form in biologic fluids such as blood, saliva, gastrointestinal contents and milk. HBGAs are synthesized from a series of precursor structures by stepwise addition of monosaccharide units via a set of glycosyltransferases that are genetically controlled and known as the ABO, Lewis, and secretor gene families.

The human HBGA system is highly polymorphic and is controlled by multiple gene families with silent alleles. The presence of such diversified molecules as HBGAs on the cell surfaces indicates a possible host defense mechanism against the changing external environment. Nevertheless, HBGAs have been linked to infection by several bacterial and viral pathogens, and may provide a "docking station" for noroviruses. That is, HBGAs can be a recognition target for pathogens and may facilitate entry into a cell that expresses or forms a receptor-ligand bond with the antigens. While the exact nature of such an interaction is not currently known, close association of a pathogen that would occur with antigen binding may play a role in anchoring the pathogen to the cell as an initial step in the infection process.

The recognition of human HBGAs by NORs is a typical protein-carbohydrate interaction, in which the protruding domain of the viral capsid protein forms an interface with the oligosaccharide side-chains of the HBGA antigens, with a wide diversity among different strains. As pathogens that replicate possibly only in the intestinal tract, NORs have developed unique strategies to overcome the host defense system. This has been shown by their genetic and structural variations, which explains why NOR-associated diseases are so common and widespread in every population worldwide.

PCT Patent Publication US2003/101176, published Dec. 2, 2003, which is incorporated herein by reference in its entirety, relates to the binding of NOR strains to ABO and Lewis HBGAs in one of several distinct histo-blood group patterns. The recognition of HBGAs by NORs is strain specific, and a number of distinct HBGA binding patterns have been identified. More binding patterns may be found, based on the diversity of NORs and the polymorphism of carbohydrates on host cell surfaces.

PCT Patent Publication US2006/138,514, published Dec. 28, 2006, which is incorporated herein by reference in its entirety, relates to a small particle, known as the P-particle, which displays enhanced binding affinity to HBGAs. The P-particle is a T=1 icosahedron built by 24 P-domain monomers that organize into 12 identical P-domain dimers. Both 12 (P-domain dimers) and 24 (P-domain monomers) are perfect unit numbers for an icosahedral symmetry that occurs frequently for plant and animal viruses. The isolated P-domain, without the S-domain or the hinge of the monomer capsid protein, can spontaneously form a T=1 icosahedral P-particle, a complex consisting of 24 P-domain monomers arranged into 12 dimers. The P-particle can bind to the corresponding HBGAs and reveals strong blocking of NOR VLP binding to the HBGAs. The spontaneous formation of P-particles has been observed with various strains of NOR, including strains VA387, MOH, and Norwalk Virus (NV). The NOR P-particle is useful in the therapeutic treatment of the NOR infection, and in creating a vaccine against NOR infection.

Both Rotaviruses (RVs) and NORs are common pathogens worldwide that incur a large burden of disease. On a worldwide basis, up to 1 billion episodes of gastroenteritis of all causes occur each year in children <5 years of age, of which 13 to 25% (~130 million episodes) are caused by RVs. RVs are the leading cause of severe diarrhea and dehydration among children and each year severe RV gastroenteritis causes 350,000-600,000 deaths in children <5 years of age. It also accounts for 2 million childhood hospital admissions with an estimated cost of over 1 billion dollars per year. On the other hand, NORs are the most important cause of non-bacterial epidemics of acute gastroenteritis, affecting individuals of all ages. NORs are highly contagious and can be spread quickly leading to large outbreaks in a variety of settings. A recent report estimated that NORs cause 1,091,000 inpatient hospitalizations and 218,000 deaths in children <5 years of age in the developing countries each year. In the USA foodborne pathogens infect an estimated 76 million people each year and are the cause of 325,000 hospitalizations. NORs alone cause $350 to $750 million in losses each year due to clinical care and lost revenue from recalled foods.

Although two new RV vaccines (Rotarix™, GlaxoSmithKline and RotaTeq®, Merck) have recently been introduced there are several issues related to the vaccine that are not yet fully resolved: a) its efficacy when vaccinated and non-vaccinated children are exposed to a wider range of RV serotypes than those found in the vaccines; b) vaccine cost and distribution costs leading to questions of how widely these vaccines will be distributed into poor countries where they are most needed; and c) the level of protection in developing countries, where mortality is highest, is still being determined. These live attenuated vaccines could possible revert or reassort to produce virulent strains. Thus, there is a need for a new generation of subunit vaccines containing highly effective neutralizing epitopes of RV. Currently, there is no treatment for NOR-associated diseases. Therefore, the development of an effective vaccine against NOR and RV, especially a single vaccine that could protect against both, would fulfill a major clinical need, further emphasizing the significant commercial potential of the P-particle vaccine platform disclosed herein.

Notwithstanding the advancements in the therapeutic treatment of and a vaccine development against NOR infections, there remains a need for improving the identification of infections caused by other virus types, the therapeutic treatment of other virus types, vaccine development against other virus types, and the development of an improved drug delivery system to target a specific tissue or organ.

SUMMARY OF THE INVENTION

The present invention relates to the discovery that a distal portion of the NOR P-domain monomer includes a peptide string into which a peptide unit of a foreign antigen, and in particular a foreign viral antigen, can be inserted. The resulting antigen-P-domain monomers can spontaneously assemble into a nanoparticle called an antigen-P-particle, typically of an octahedral form, that consists of 24 of the antigen-P-domain monomers arranged into 12 dimers. This P-particle is easily produced in *E. coli*, extremely stable, and highly immunogenic. There are three surface loops per P-domain monomer, making a total of 72 loops per particle, which are potential sites for foreign antigen presentation for immune-enhancement. The antigen-P-particles form spontaneously, and have the foreign antigen(s) presented on the distal portions of the P-domain monomers. This process of forming antigen-P-particles can exchange or equilibrate dynamically, depending on the concentration of the antigen-P dimer. The antigen-P-particle is useful in raising antibodies to the foreign viral antigen and also in creating a vaccine for such foreign virus infections.

A first aspect of the present invention relates to a modified NOR P-particle for use as a platform to present antigens of various infectious pathogens, thus providing new vaccine strategies against these diseases. The platform is also useful for development of vaccines or as carriers of drugs or drug delivery vehicles for treatment of non-infectious diseases, including cancers, allergies, and autoimmune diseases. In comparison to a number of other vaccine platforms, the antigen-P-particle system has many advantages, including high yield and low cost of production, with simple purification procedures and high efficiency of the antigen presentation.

The antigen-P-particle of the present invention is formed by the protruding (P) domain of the NOR capsid, and contains 24 copies of the P-domain monomers, which are arranged in dimers. The molecular weight and size of the antigen-P-particle, of about MW=830 kDa and (I)=20 nm, is an effective size for a subunit vaccine. Foreign antigens are inserted into one or more of three (3) surface loops present on each P-domain monomer, thereby presenting up to 72 copies of the foreign antigen on the surface of each antigen-P-particle. The multiplicity of foreign antigens on a single antigen-P-particle enhances greatly the antigenicity and immunogenicity of the foreign antigens. Various types and sizes of foreign antigens, from small polypeptides to large proteins, can be inserted into any one or more of the three surface loops, including as representative examples of foreign antigens, the His-tag (7 histidines), the T-cell epitope of mouse cytomegalovirus (9 aa), the Epi8 antigen of *Pseudomonas* (10 aa), VP8 of rotavirus (RV) (159 aa), and the green fluorescent protein (238 aa).

The NOR P-particle is highly stable and tolerates a wide range of physio-chemical conditions. Most importantly, unlike many other recombinant subunit vaccines that require a eukaryotic system for production, the antigen-P-particle, like the wild type NOR P-particles, can be readily produced in *E. coli* and yeast, or other bacterial sources, with extremely high yields and simple purification procedures.

A second aspect of the present invention is a user-friendly means for inserting candidate foreign antigens into the one or more of the surface loops present on each P-domain monomer by insertion of convenient cloning cassettes. Cloning cassettes typically include one or more, and typically at least one pair of specific recognition nucleotide sequences, also known as restriction sites or restriction recognition sites, into the one or more loops of the P-domain vectors. Restriction sites are specific sequences of nucleotides that are recognized by restriction enzymes. The sites are generally palindromic (because restriction enzymes usually bind as homodimers), and a particular restriction enzyme typically cuts a specific DNA sequence between two nucleotides within its recognition site, or somewhere nearby. For example, the common restriction enzyme EcoRI recognizes the palindromic sequence GAATTC and cuts between the G and the A on both the top and bottom DNA strands, leaving an overhang (an end-portion of a DNA strand with no attached complement) on each end. This overhang or "sticky end" can then be used to add or ligate (via DNA ligase) a piece of DNA with a complementary overhang (e.g. another EcoRI-cut piece of DNA). The use of restriction sites in one or more of the surface loops present on each P-domain monomer allows substitution of a foreign antigen contained within a cloning cassette into any one or more of the surface loops, as well as two or more different foreign antigens or other cloning cassettes into different ones of the three loops of the P-domain monomer.

Another aspect of the present invention is the formation of antigen-P-particles by the spontaneous assembly of 24 P-domain monomers, as 12 pairs of dimers. When all of the P-domain monomers are the same, the antigen-P-particle is termed a homogenous P-particle.

Another aspect of the present invention is the formation of heterogenous antigen-P-particles, including two or more differently-modified antigen-P-domain monomers, or at least one diversely-modified antigen-P-domain monomer and the wild-type P-domain monomer. The diversely-modified antigen-P-domain monomers or wild-type P-domain monomers can be used in any ratio (molecular or weight ratio), to obtain a wide variety of antigen-P-particles.

Another aspect of the present invention is the use of the antigen-P-particles as candidate vaccines to provide immune protection against viruses, with specific viral antigens inserted into at least one of the surface loops of each P-domain monomer within the P-particle, including for example rotavirus (RV) antigens.

Another aspect of the invention relates to a method of protecting humans from a viral disease, the method comprising administering to a human an immunizing amount of the antigen-P-particle having a specific viral antigen inserted into at least one of the surface loops of the P-domain monomer within the P-particle as described herein in a sterile, nontoxic pharmaceutically acceptable carrier, wherein the antigen is the viral antigen.

Another aspect of the invention relates to a method of inducing an immune response in an individual against a viral disease, the method comprising the step of orally or parenterally administering to an individual at least one immunologically effective dose of a composition comprising the antigen-P-particle described herein and a pharmaceutical carrier, wherein the antigen is the viral antigen, and wherein the dose is effective in inducing the immune response in the individual.

Another aspect of the present invention is an antigen-P-particle vector/vaccine platform kit.

Another aspect of the present invention relates to introduction of restriction sites, including unique or rare restriction sites, into the cloning cassette of the one or more fully-exposed loops of the P-domain monomer. Regarding the insertion of cloning cassettes containing restriction sites, it is recommended to avoid the insertion of a protease recognition sequence into the cloning cassette of the loops. For example, the BgIII site (AGATCT) encodes a di-amino acid restriction site which is a typical trypsin cutting site and should be avoided.

Another aspect of the present invention relates to modifications of one or more of the loops, including by adding a spacer or arm to extend the exposure of a loop, in order to accommodate optimally certain foreign antigens.

Another aspect of the present invention relates to the design of multiple insertions of different antigens, to prevent a large antigen, such as the RV VP8, from covering a neighbor loop having a smaller foreign antigen, which may make the presentation of a small epitope on this loop difficult.

Another aspect of the present invention relates to an insertion of a ligand or signal peptide into one or more surface loops of the P-domain monomer, resulting in a substituted P-particle with the inserted ligands or signal peptides on one or more of the distal surfaces. This ligand or signal peptide can then allow the substituted P-particle to target the corresponding receptor in specific organs or tissues and then travel to those locations. For example, a substituted P-particle with the peptide CNGRC (SEQ ID NO:4; 5 amino acids) may be able to travel to the tumor tissue (i.e. carcinoma) where the receptor (CD13) of CNGRC is heavily expressed.

Another aspect of the present invention relates to a substituted P-particle monomer, and dimers and P-particles thereof, having a conjugate of a drug inserted into a loop of the P-particle through surface-exposed lysines and cysteines by chemical reaction. In this case, the substituted P-particle will be used as a carrier for drugs.

Another aspect of the present invention relates to a substituted-P-monomer, and dimers and P-particles formed therefrom, with a ligand or signal peptide inserted in at least one of the surface loops and with a conjugate of a drug inserted in at least one of the surface loops. These substituted P-particle provide a drug delivery system to target the drug to specific tissues or organs with illnesses.

Another aspect of the present invention is a gene sequence of the modified genetic code of the modified- or antigen-P-domain monomer.

Another aspect of the present invention is a reproducing biological entity (e.g., *E. Coli*) with the modified genetic code of the modified- or antigen-P-domain monomer.

While the nature and advantages of the present invention will be more fully appreciated from the following drawings and detailed description, showing the contemplated novel construction, combinations and elements as herein described, and more particularly defined by the appended claims, it is understood that changes in the precise embodiments of the present invention are meant to be included within the scope of the claims, except insofar as they may be precluded by the prior art.

FIG. 15 illustrates responses of mice to the P-particle presented short peptides. (A) immune reactivity of mouse sera (n=5) after immunization with equal amount of the P-particle-His-tag chimera (PP-His, blue), P dimer-His-tag chimera (PD-His, purple), or wild type P-particle (WT PP, control, black), respectively, to recombinant His-tagged-α-fucosidase of *T. Maritima* in EIAs. (B) antibody titers of the sera in (A) were determined by an endpoint dilution approach. (C) to (F), antibody responses of mice to unexposed short peptides in the P-particle. (C) immune reactivity of mouse sera (n=5) after immunization with the P-particle containing a buried peptide CDCRGDCFC(PP-CDCRGDCFC) to the CDCRGDCFC-tagged maltose-binding protein (MBP) (to CDCRGDCFC, SEQ ID NO:5, purple) and wild type P-particle (to WT PP, positive control, green) in EIAs. The immune reactivity of the mouse sera after immunization with the P-particle-His-tag to the His tagged α-fucosidase of *T. Maritima* if (A) (PP-His to His-tag, blue) was included for comparison. (D), antibody titers of the sera in (C) were determined by an endpoint dilution approach. (E), immune reactivity of mouse sera after immunization with P-particle containing a buried peptide CNGRC to the CNGRC-tagged MBP (to CNGRC, SEQ ID NO:4, purple) and wild type P-particle (to WT PP, positive control, green). The immune reactivity of the mouse sera after immunization with the P-particle-His tag to the His tagged α-fucosidase of *T. Maritima* of (A) (PP-His, blue) was included for comparison. (F), antibody titers of the sera in (E) were determined by an endpoint dilution approach. Different antigens [His-tagged-α-fucosidase for (A) and (B), CDCRGDCFC-tagged MBP for (C) and (D), CNGRC-tagged MBP for (E) and (F), and wild type P-particle for (C) to (F)] at 5 ng/μl were coated on microtiter plates for EIA assays. Corresponding sera at indicated dilutions were used to measure the immune reactivity. * $P<0.05$.

FIG. 16 illustrates the production and analysis of the P-particle-VP8 chimera. (A) the expression construct of the P-particle-VP8 chimera based on vector pGEX-4T-1 containing the P domain-encoding cDNA sequences. The rotavirus (Wa) VP8 antigen was inserted in loops 2 of the P domain between T368 and L375 through the cloning cassette with enzyme sites Spe I and Cla I/EcoRI. Circled C represents the cystein containing peptide (CDCRGDCFC; SEQ ID NO:5). (B) expression and purification of the P-particle-VP8 chimera. SDS PAGE analysis revealed that GST-P-VP8 fusion protein (GST fusion) is ~80 kDa (left panel). Digestion of the fusion protein by thrombin results in GST (~27 kDa) and the P-VP8 chimera (~52 kDa) (middle panel). The free P-VP8 chimera can also be released from the purification beads by thrombin digestion (right panel). Lanes M were prestained protein markers with bands from top to bottom representing 113, 92, 50, 35, 29, 21 kDa. (C) the elution curve of the gel filtration chromatography of the thrombin-released P-VP8 protein through the size exclusion column Superdex 200. A SDS PAGE analysis of the fractions of the peaks is shown on the top. The column was calibrated with blue dextran 2000 (~2000 kDa, void), wild type P-particle (~830 kDa), and wild type P dimer (~70 kDa), respectively. The single major peak near void indicated that almost all P-VP8 protein formed chimeric P-particle. (D), the P-VP8 protein (left panel) reacted to antibodies against rotavirus VP8 (middle panel) and norovirus VLP (right panel).

FIG. 17 shows the immune responses of mice to P-particle presented VP8s. Equal molar amount of the P-particle-VP8 chimera and free VP8 were used to immunize mice, either intranasally without an adjuvant (A and B, n=5-7), or subcutaneously with the Freund's adjuvant (C, n=6-7). Free VP8 and GST were used as antigens for antibody titer determination in an EIA. (A and B) antibody titers of mouse sera against VP8/GST after immunization with free VP8 antigen (free VP8) and the chimeric P-particles (PP-VP8) containing VP8s of Wa (A) and DS1 (B), respectively. (C), antibody titers against VP8 after immunization with free VP8 antigen (free VP8) and the chimeric P-particle (PP-VP8) containing VP8 of Wa strain. The co-purified GST served as internal control. ** $P<0.001$.

FIG. 18 illustrates the neutralization to rotavirus by mouse sera induced by immunization with P-particle-VP8 chimeras. (A) mouse sera from mice immunized intranasally with P-particle-VP8 (Wa, [P]8) chimera without an adjuvant shows strong neutralization to the same Wa strain (PP-VP8 sera, blue), while sera from mice immunized with free VP8 show significantly lower neutralization (VP8 sera, black). Sera from mice receiving no antigen served as negative control (control sera, purple). (B) sera from mice immunized with P-particle VP8 (DS1, [P]4) chimera shows weak cross neutralization to Wa (PP-VP8 sera, blue), whereas sera from mice immunized with free VP8 of DS1 (VP8 sera) and the negative control sera did not show neutralization (black and purple). (C), immune reactivity against VP8 of sera from mice immunized with free Wa VP8 (VP8 sera, black) and P-particle-VP8 (Wa) chimera (PP-VP8 sera, blue) subcutaneously with the Freund's adjuvant. Both antigens induced similar antibody responses to free VP8 (Wa). Sera without antigen serves as negative control (control sera, purple). (D) the sera from (C) induced by immunization of mice with P-particle-VP8 chimera showed significantly higher neutralization titers to rotavirus (Wa) (PP-VP8 sera, blue) than that of sera induced by immunization with free VP8 (VP8 sera, black). Control sera from mice receiving no antigen served as a negative control (control sera, purple). The star symbols indicate the P values between the neutralization of the sera induced by the two forms of VP8: * $P<0.05$; , $P<0.005$, and *, $P<0.0005$.

FIG. 19 illustrates protection after immunization of mice with P-particle-VP8 chimeric vaccine against a mouse rotavirus infection. Rotavirus shedding (μg/ml) of mice was measured after vaccination with four different vaccines and challenged by murine rotavirus (EDIM). WT PP, mice were vaccinated with wild type norovirus P-particle (vector control, n=7). PP-hVP8, mice were vaccinated with P-particle-VP8 (Wa) chimera (n=5). Free mVP8, mice were vaccinated with free murine VP8 (EDIM) antigen (n=5). PP-mVP8, mice were vaccinated with P-particle-VP8 (EDIM) chimera (n=5). Data calculation and statistic analysis are shown in Table 1.

Figure 20:
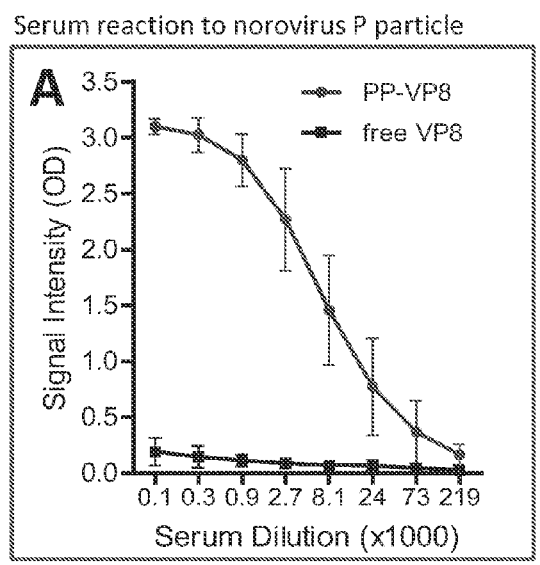
Figure 20:
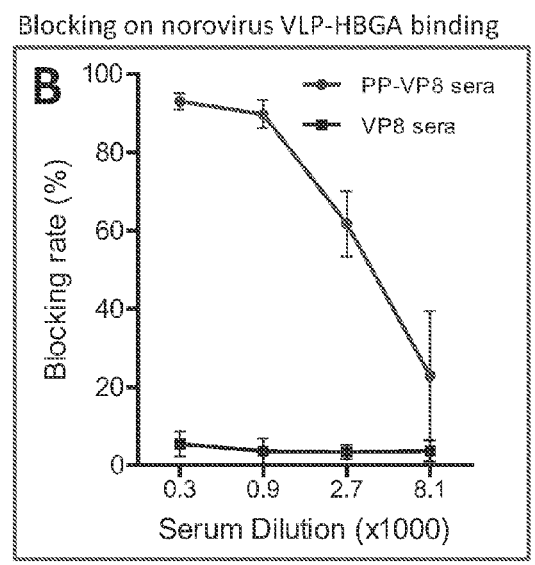

FIG. 20 shows antibody induced by immunization with P-particle-VP8 chimeras block binding of norovirus VLP to HBGA receptors. (A) mouse sera after immunization with the P-particle-VP8 (Wa) chimeras reacted strongly to norovirus P-particle (PP-VP8), while the free VP8 induced sera did not show this reactivity (free VP8). (B) mouse sera from (A) blocked binding of norovirus VLP to HBGA receptor (type A saliva, PP-VP8 sera, blue), while sera obtained after immunization with free VP8 did not show this blockade (VP8 sera, black).

DETAILED DESCRIPTION OF THE INVENTION

As used herein, the terms "Norovirus," "NOR", "Norwalk-like virus," or "NLV" refer to any virus of the Norovirus family, and includes, without limitation, the following: Norwalk Virus ("NV"), MOH, Mexico, Va. 207, VA 387, 02-1419, C59, VA 115, Hawaii, Snow Mountain, Hillington, Toronto, Leeds, Amsterdam, Idaho Falls, Lordsdale, Grimsby, Southampton, Desert Shield, Birmingham, and White Rivercap.

As used herein, the terms "P-domain monomer" and "P-particle" refer to a wild type Norovirus P-domain monomer and wild type Norovirus P-particle, respectively.

As used herein, the terms "modified P-domain monomer" and "modified P-particle" refer to a Norovirus P-domain monomer and P-particle (respectively) that has been modified to insert one or more restriction sites (typically in pairs) into one or more of three surface loops present on each P-domain monomer by molecular cloning, thereby creating cloning cassettes in the surface loops which allow for the later insertion of foreign antigens, ligands, drug conjugates, or signal peptides.

As used herein, the terms "substituted P-domain monomer" and "substituted P-particle" refer to a Norovirus P-domain monomer and P-particle (respectively) that includes at least one of a foreign antigen, ligand, drug conjugate, or signal peptide inserted into one or more of three surface loops present on each P-domain monomer by molecular cloning.

As used herein, the terms "antigen-P-domain monomer" or "antigen-Norovirus P-domain monomer" refer to a substituted P-domain monomer in which a foreign antigen has been inserted into one or more of the three surface loops present the P-domain monomer.

As used herein, the terms "antigen-P-particle" or "antigen-Norovirus P-particle" refer to a substituted P-particle in which a foreign antigen has been inserted into one or more of the three surface loops present each P-domain monomer.

Four unique, noninfectious NOR particles, namely virus-like particles (VLPs), S-particles, P-particles, and small P-particles are viral protein cages that represent excellent candidates for engineering multifunctionality, and are described in Tan et al., 2004, "The P-domain of norovirus capsid protein forms dimer and binds to histo-blood group antigen receptors", J Virol 78:6233-42, and Tan et al., 2005, "The p domain of norovirus capsid protein forms a subviral particle that binds to histo-blood group antigen receptors", J Virol 79:14017-30, the disclosures of which are incorporated herein by reference in their entirety. These particles have molecular masses ranging from 420 kDa (small P-particle) to 10.5 mDa (VLP) and sizes from 14 to 37 nm. The NOR VLP is composed of 180 full capsid proteins (VP1), while the three subviral particles are made from a portion of the VP1. The S-particle from the shell (S) domain, the P-particle from the protruding (P) domain, and the small P-particle from the same P-domain but with an additional flag-tag at the N-terminus. All these particles assemble spontaneously when the proteins are expressed in vitro, as described in Tan et al., 2004, supra; Tan et al., 2004, "E. coli-expressed recombinant norovirus capsid proteins maintain authentic antigenicity and receptor binding capability", J Med Virol 74:641-9; and Xia et al., 2007, "Norovirus capsid protein expressed in yeast forms virus-like particles and stimulates systemic and mucosal immunity in mice following an oral administration of raw yeast extracts", J Med Virol 79:74-83, the disclosures of which are incorporated herein by reference in their entirety.

Figure 2:
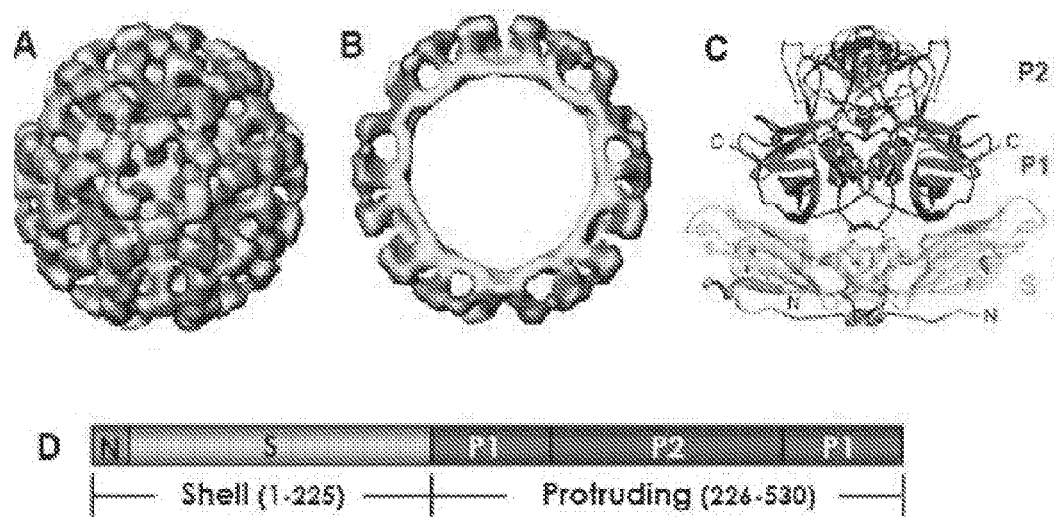

The wild-type NOR capsid is composed of a single major structural protein of 55-60 kDa (VP1) that self-assembles into virus-like particles (VLPs) when expressed in insect cells (FIG. 2). VLPs are morphologically and antigenically identical to the native viral particle, but are not infective. On the basis of the X-ray crystallographic structure of Norwalk virus, capsids are composed of 90 dimers of VP1 and exhibit T=3 icosahedral symmetry. Each VP1 monomer (530 amino acids [aa]) contains a short N-terminal region (aa 1 to 49), followed by a shell (S) domain (aa 50 to 225) and a protruding (P) domain that can be divided into two subdomains: P1 (aa 226 to 278 and 406 to 520) and P2 (aa 279 to 405). The N-terminal/shell (N/S) domain forms the inner core of the capsid and is the most conserved part of VP1, while the P domain forms the protruding arches of the capsid and is more diverse. The P2 subdomain, which is located at the surface of the capsid, contains the highest degree of variability in the genome among NOR strains. It contains the determinants of strain specificity, receptor binding, and potential neutralizing antibody recognition sites.

According to the atomic structures, the shell (S) and protruding (P1, P2) domains (FIG. 2) of the NOR capsid protein are linked by an 8-10 amino acid hinge. The receptor-binding region of the capsid protein (VP1) of the P-particle has been mapped as described in Tan et al., 2004, "The P domain of norovirus capsid protein forms dimer and binds to histo-blood group antigen receptors"% J Virol 78:6233-42, the disclosure of which is incorporated herein by reference in its entirety.

NORs are known to recognize human histo-blood group antigens (HBGAs) as host receptors for infection. Expression of the S-domain forms a smooth particle that does not have the function of binding to host receptors, while expression of the P-domain with the hinge forms a dimer with receptor-binding function but the binding affinity is low. When the P-domain is expressed without the hinge, it spontaneously forms a subviral P-particle (FIG. 1) with significantly increased receptor binding affinity similar to that of VLPs. The P-particle consists of 24 P-domain monomers arranged into 12 dimers. The P-particle can bind to corresponding HBGAs and reveals strong blocking of NOR VLP binding to the HBGAs. The spontaneous formation of P-particles has been observed with various strains of NOR, including strains VA387, MOH, and Norwalk Virus (NV). These P-particles revealed a ring-shape image with a center cavity under electron microcopy (EM) and formed a single peak in gel filtration with a molecular weight of ~830 kDa. The P-particle is very stable and can be produced easily in both E. coli and yeast expression systems with high yield, as described in Tan et al., 2005, "The p domain of norovirus capsid protein forms a subviral particle that binds to histo-blood group antigen receptors", J Virol 79:14017-30, and Tan et al., 2006, "C-terminal arginine cluster is essential for receptor binding of norovirus capsid protein", J Virol 80:7322-31, the disclosures of which are incorporated herein by reference in their entirety.

The NOR P-particle is a common feature for NORs, as demonstrated by construction of NOR P-particles from different genotypes of the two major genogroups of human NORs. So far over 40 NOR P-particles have been constructed representing different NOR genotypes, including GI-1 (Norwalk virus), GI-4 (Koblenz433), GI-8 (Boxer), GD-2 (Melksham), GD-3 (Brattleboro321), GII-4, GD-5 (MOH), GII-9 (VA207). For the dominant NOR types (GII-4) that are responsible for 65-85% of worldwide NOR gastroenteritis, 25 P-particles have been made. This represents 25 strains that have circulated during the past 25 years.

Figure 1:
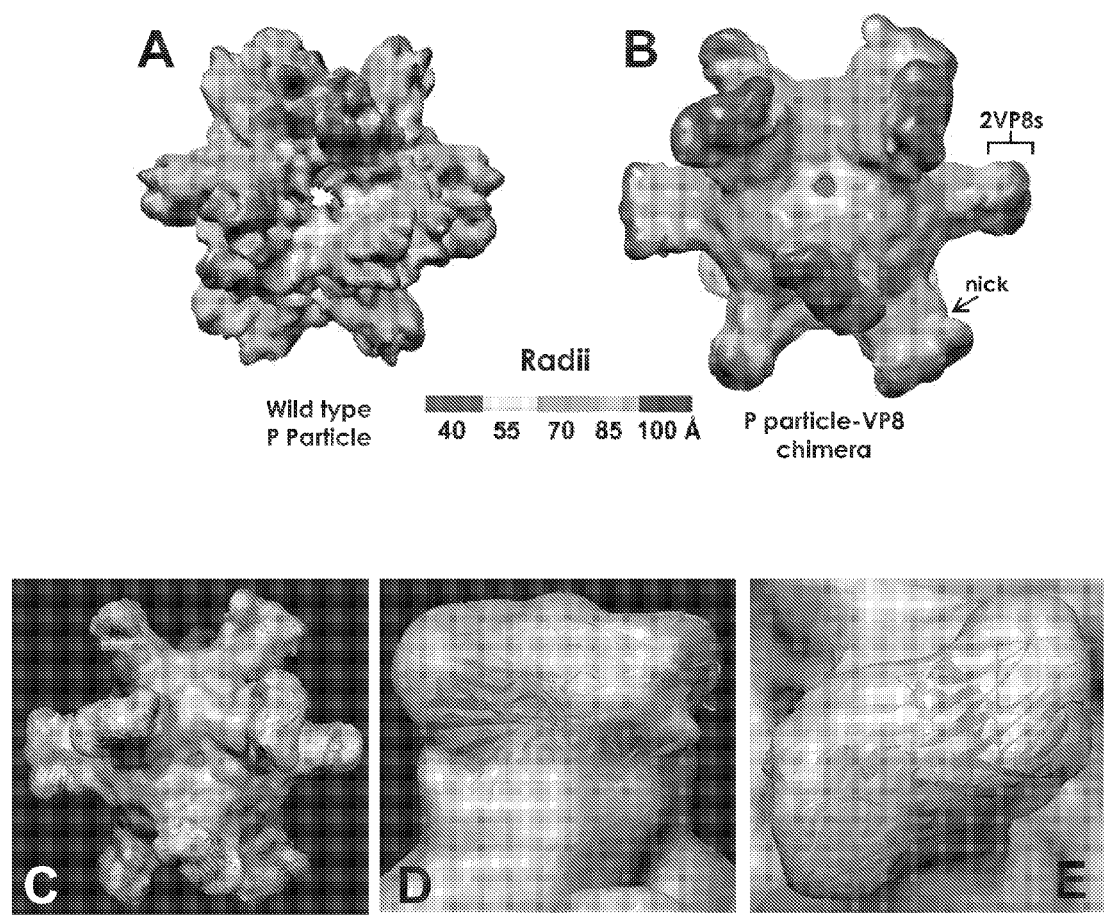
FIG. 1 shows Cryo-EM structure of the P-particle-VP8 chimera. (A) a wild type P-particle. (B) a P-particle-VP8 chimera. Compared to the wild type P-particle the chimera shows extended protrusions with nicks in the middle, suggesting the boundary between the P2 subdomain and the inserted VP8 antigen. The radii of the particles in (A) and (B) are ind inserted in loops 2 between the N372 and D374. pGEX-4T-1 is a expression vector of the GST-gene fusion system. Circled C represents a cystein containing peptide (CDCRGDCFC; SEQ ID NO:5). (B) a distal end of a protrusion of the P-particle in crystal structure (cartoon model) indicates the location of two N373 (dot models in gray and cyan), where the inserted His-tags are expected to be located. (C) expression and purification of the P-particle-His-tag chimera. SDS PAGE analysis revealed that GST-P domain-His tag fusion protein (GST fusion) is ~52 kDa. Digestion of the fusion protein in solution by thrombin resulted in GST (~27 kDa) and the P domain-His tag chimera (PD-His-tag) (~35 kDa, left panel). The P domain-His tag chimera can also be released from the purification resin by thrombin digestion (right panel). M is prestained protein marker with bands from top to bottom representing 113, 92, 50, 35, 29, 21 kDa. (D) the elution curve of a gel filtration chromatography of the thrombin-released P-domain-His tag protein using the size exclusion column Sperdex 200. Three major peaks representing void, P-particle-His-tag and P dimer-His-tag were indicated, respectively. The sizes of these three peaks were calibrated with blue dextran 2000 (~2000 kDa, void), wild type P-particle (~830 kDa), and wild type P dimer (~70 kDa), respectively. (E) the fractions of the gel filtration chromatography (D) were analyzed by SDS PAGE.
Figure 3:
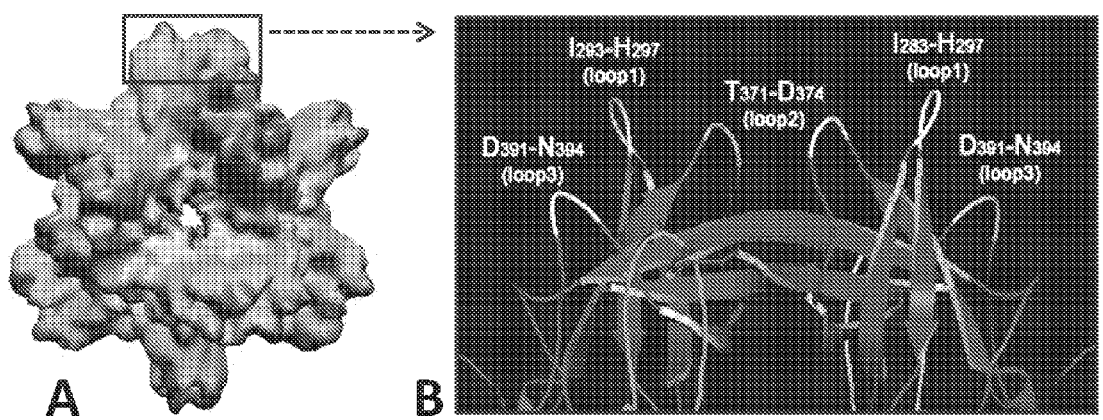

The 3-D structure of the P-particle has been reconstructed by cryo-EM to a resolution of 7.6 Å, as shown in FIGS. 1 and 3. The P-particle is in an octahedral symmetry containing 24 P-domain monomers organized in 12 P dimers. There is a cavity at the center of the P-particle. The orientation of the P dimers is similar to those in the wild-type NOR capsid, in which the P1 subdomain is inward with respect to the center of the cavity, while the P2 subdomain is outward with respect to outermost surface of the P-particle. Fitting-in of the crystal structure of the P dimer (FIG. 4) into the density map of the cryo-EM of the P article indicates that the HBGA receptor binding interfaces are located at the outermost surface of the P-particle. This is consistent with the observation of P-particle retaining a strong binding function to HBGA receptors.

Figure 4:
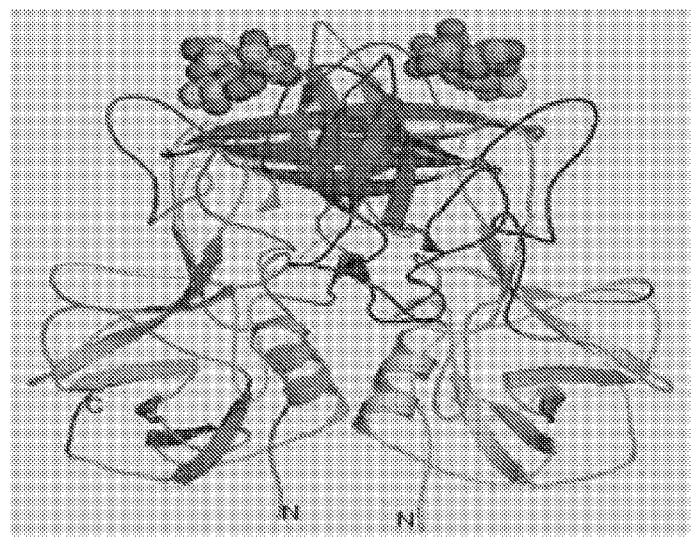
Figure 5:
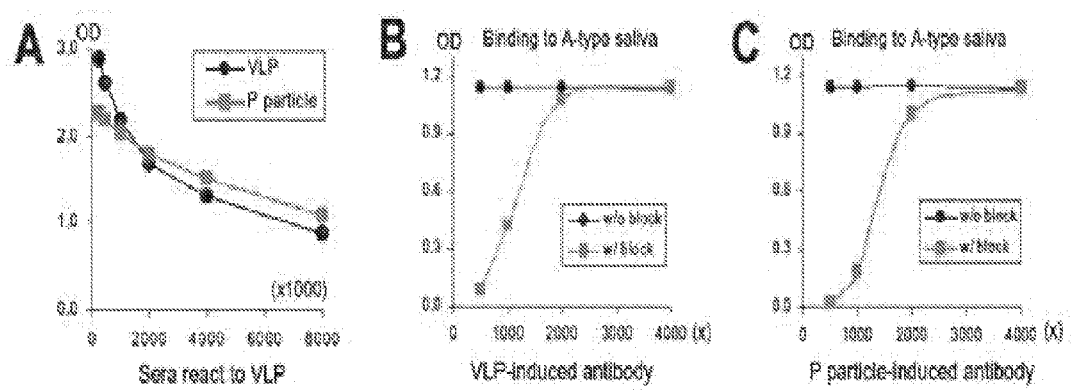

The atomic structures of the P dimers have been elucidated in the prototype Norwalk virus and a predominant GII-4 strain (VA387) by X-ray crystallography (FIG. 4). These crystal structures fit well into density maps of the cryo-EM of the P-particle (FIG. 1). Three surface loops were identified at the furthermost end of each P monomer, corresponding to the top of the arch-like P dimer (6 surface loops/P dimer, FIG. 3), or the outermost surface of the NOR capsid and P-particle. These surface loops provide excellent sites for foreign antigen presentation and the detailed crystal structures provide a solid foundation for the structure-based design of the P-particle vaccine platform disclosed herein.

The P-particle relies on its outermost surface to bind to HBGA receptors. When any one or more of a restriction enzyme site, an antigen, a ligand, a signal peptide or a drug conjugate is inserted into a surface loop of a wild-type P-domain monomer, it will cover the outermost part of the formed P-particle, either partially or fully depending on the size of the restriction enzyme site, antigen, ligand, signal peptide or drug conjugate, and can either hinder access to one or more of the modified or substituted loops, or change the protein structure of the modified or substituted loops, whereby the formed P-particle can lose its capability of binding to the HBGA receptors. We have not yet systematically analyzed how much altering of a loop is needed before the P-particles no longer bind the HBGAs. However, we do know that, when restriction sites are added to the middle loop 2 of the P-domain monomers, the modified P-particle will not bind to HBGAs.

Identification of the viral receptor binding interfaces has been shown by crystallization of the P dimers in complex with an A- or a B-trisaccharide (noroviral receptors) in Norwalk virus and VA387, as shown in FIG. 4. As illustrated, FIG. 4 shows the crystal structure of NOR P dimer (ribbon model) associated with a B-trisaccharide complex (spherical model). The receptor-binding interfaces are located at the top of the arch-like P dimer equivalent to outermost surface of the NOR capsid and the P-particle. Extensive hydrogen bonding networks between the trisaccharides and the amino acids of the P dimer are observed. The importance of these amino acids, which were predicted to interact with viral receptors, have been proven by site-directed mutagenesis, as described in Tan et al., 2008, "Elucidation of strain-specific interaction of a GII-4 norovirus with HBGA receptors by site-directed mutagenesis study", Virology 379:324-334, the disclosure of which is incorporated herein by reference in its entirety.

Among the four NOR particles (VLPs, S-particles, P-particles, and small P-particles), the P-particle is the most stable and easily produced. It is highly immunogenic and tolerates a wide range of temperatures, pHs, and chemical and physical conditions. The 3-D structure of the P-particle by cryo-EM (FIG. 1) and the atomic structure of the P dimer (FIG. 2) show that three surface loops are highly exposed on the outermost surface of each of the 24 monomers or 12 P dimers of the P-particle (FIGS. 1, 3 and 4), as described in Cao et al., 2007, "Structural basis for the recognition of blood group trisaccharides by norovirus", J Virol 81:5949-57, and Tan, 2008, "Noroviral P-particle: Structure, function and applications in virus-host interaction", Virology, Vol. 382, Issue 1, 5 Dec. 2008, Pages 115-123, the disclosures of which are incorporated herein by reference in their entirety. Structure-based sequence alignment suggests that these exposed loops tolerate large sequence insertions.

In an aspect of the present invention, when a protein or polypeptide antigenic epitope is inserted at or within one of these loops, namely Loop 1 (1293-H297, SEQ ID NO:1), Loop2 (T371-D374, SEQ ID NO:2), or Loop 3 (D391-N394, SEQ ID NO:3), the spontaneous self-assembly of the antigen-P-domain monomers or dimers presents twenty-four (24) of the antigenic epitopes on the surface of the assembled antigen-P-particle. This feature of the invention provides advantages for antigen presentation, and therefore vaccines, as discussed below. The elucidated atomic structure of the P dimer has thus provided solid and detailed information of structure-based design for such antigen insertions.

Like the wild-type P-domain monomers and dimers, the process of formation of the antigen-P-domain monomers into dimers, and dimers into the antigen-P-particle, can exchange or equilibrate dynamically, depending on the concentration of the P dimer. Also like the wild-type P-domain monomers and dimers, when a cysteine is linked to the end of the antigen-P-domain monomer, the resulting antigen-P-particles become much more stable and much less concentration-dependant on the antigen-P-domain monomer than those without the cysteine tail. Each antigen-P dimer should have the same orientation in their interaction with five surrounding antigen-P dimers, forming a pentagon along the five-fold axis. As a consequence, the outer layer of the antigen-P-particle is formed by the P2 subdomain, similar to the arch structure of the norovirus capsid, while the inner layer is made by the P1 subdomain, providing support to the P2 arch. Like other icosahedral viral particles there should be a cavity inside the antigen-P-particle.

Also like the wild-type P-domain monomers and dimers, antigen-P-domain monomers and dimers of the present invention can be denatured by well known means, to prevent their in vitro spontaneous formation into antigen-P-particles. Likewise, antigen-P-particles of the present invention can be denatured to spontaneously disassemble into the respective antigen-P-domain monomers and dimers. This permits in vitro blending or mixing of formation of antigen-P-domain monomers of diverse antigenic type, optionally with wild-type P-domain monomers, into a variety of molecular ratios, that can then be spontaneously formed into antigen-P-particles when the denaturing influence is removed.

The substituted or antigen-P-particle of the present invention, like the wild-type NOR P-particle, is an attractive candidate for antigen display because it is stable and easily produced in *E. coli* and yeast, by well known methods such as those described in Tan et al., 2004, J Virol 78:6233-42, and Tan et al., 2005, Virol 79:14017-30, supra. While the prior art chimera FHV particles of Manayani et al. and chimera CPMV particles of Chatterji et al. infect insects and plants, respectively, with unknown effects on humans, the non-infectious wild-type NOR P-particle is derived from a human virus, and has been identified as a candidate human vaccine.

A number of unique features make the antigen-P-particles of the present invention, like the wild-type NOR P-particle, a valuable commercial product as a vaccine platform. First, the base NOR P-particles are multivalent with a near ideal size (~840 kDa, Φ=20 nm) for a subunit vaccine, and are much easier to make than the full-size virus-like particle (VLP) and much more immunogenic than single polypeptide or protein antigens. Second, the antigen-P-particles can be easily produced in *E. coli* with high yield and low cost, which is particularly useful for developing countries. Third, the multiple (three) surface loops of the P-domain monomer and their high capacity for insertion of foreign antigens (up to at least ~238 aa) allow multiple insertions of different antigens. Thus the resulting chimeric substituted P-particle vaccines can offer broad application against many infectious and even non-infectious diseases. Fourth, only a few simple steps of genetic engineering are needed to generate a homogenous chimeric substituted P-particle that contains at least 24 copies of the inserted foreign antigen. Thus, these vaccines can be rapidly developed, which may be particularly useful for the rapidly changing viral families such as influenza viruses. Fifth, P-domain monomer vectors that have cloning cassettes in the surface loops, including restriction sites, provide a user-friendly vector and a convenient vaccine platform. And sixth, the antigen-P-particle is an excellent candidate vaccine for both human NORs against diarrhea and other infectious diseases.

In addition to major infectious diseases, the P-domain vectors and P-particle vaccine platform may also be valuable for antigen presentation and/or as carriers of drugs or drug delivery vehicles for treatment of non-infectious diseases, including cancers, allergies, autoimmune diseases. In one embodiment, a drug can be inserted into a loop of the P-particle through surface-exposed lysines and cysteines by chemical reaction. In this case, the substituted P-particle will be used as a carrier for drugs. In another embodiment, a ligand or signal peptide can be inserted in at least one of the surface loops, and a conjugate of a drug can also be inserted in at least one of the surface loops. These substituted P-particles provide a drug delivery system to target the drug to specific tissues or organs.

The P-particles of the invention can be combined with other drug delivery approaches to further increase specificity and to take advantage of useful advances in the art. One example would encompass prodrugs which are biologically inactive unless and until pathogen infection, or specific chemical or enzymatic cleavage, converts such prodrugs into an active drug form inside a phagocytic mammalian cell. Such an embodiment could specifically involve developing a prodrug-P-particle in which the prodrug is only activated in cells infected with a particular microorganism, or in cells afflicted with a particular tumor.

The unique features of the P-particle vectors allow the vaccine platform to have broad applications. It can be used to produce many vaccines with known protective epitopes. Therefore, application of the P-particle vector vaccine platform could potentially benefit a wide range of clinical conditions. In addition, the flexibility of this nanoparticle platform can be easily extended. For example, the particle could be developed so that one surface loop of the P-domain monomer or P-particle expresses a signal peptide (a ligand) that homes the P-particle to a certain tissue or organ with a specific receptor, while the vaccine or drug can be linked to a second surface loop to be delivered to produce effects. For example, a substituted P-particle with the peptide CNGRC (SEQ ID NO:4; a chain of 5 amino acids) may be able to travel to the tumor tissue (i.e. a carcinoma), where the receptor (CD13) of CNGRC is heavily expressed. The peptide moiety CNGRC, a ligand for the membrane-bound metalloprotease CD13, can bind to endothelial cells of the angiogenic vasculature that express CD13, inducing apoptosis in endothelial cells expressing CD13, thereby inhibiting tumor-associated angiogenesis.

Further, vaccines of several valencies can be created so that 2 or more loops express different antigens from the same or different pathogens. Substituted P-particles can be assembled from a mixture of different antigen-P-domain monomers, including wild-type P-domain monomers and antigen-P-domain monomers, to form a heterogenous antigen-P-particle. The diverse foreign antigens can be inserted into the same loop or a different one of the three loops, to provide a wide variety of heterogenous antigen-P-particles. Therefore, the commercial value of the P-particle and P-domain monomer vector platform are extensive.

An embodiment of the present invention can include an antigen-P-particle for use as a vaccine against NORs and rotaviruses (RVs). One example of the antigen-P-particle is a RV VP8-P-particle chimera. Both rotaviruses (RVs) and NORs are common pathogens worldwide that incur a large burden of disease. This antigen-P-particle provides an effective vaccine against NOR and RV in a single vaccine, without the risk of a possible reversion or reassortment to produce a virulent strain.

The wild-type P-domain monomers can be prepared, prior to modification of one or more of the loops, by the addition of cysteines at either end of the P-domain to enhance and stabilize P-particle formation, and by the addition of a short peptide (CDCRGDCFC, SEQ ID NO:5) to the C-terminus of the P-domain, to affect resistance to trypsinization that may destabilize the P-particles. Also, an intact C-terminus of the P-domain monomer is required for P-particle formation, and the arginine-cluster at the C-terminus is important for P-particle formation and stability as a vaccine platform.

Figure 6:
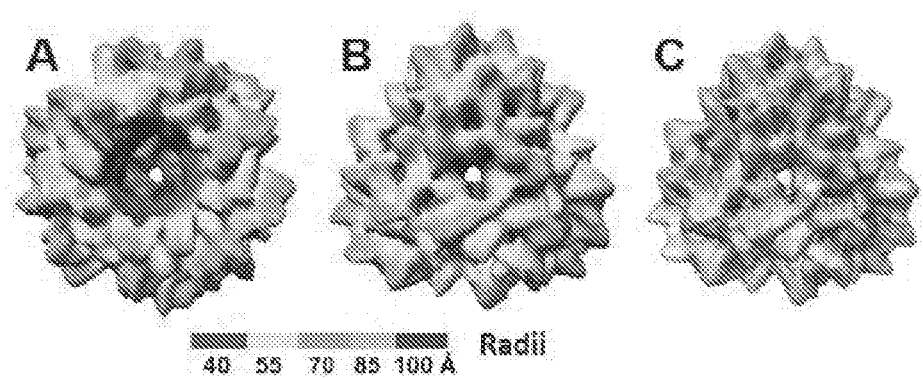

The NOR P-domain monomer also formed another complex called the small P-particle when a small peptide tag (DYKDDDDK, SEQ ID NO:6, FLAG-tag) was attached to the C-terminus of the P-domain. This small P-particle reveals a tetrahedral symmetry containing 12 P monomers organized in 6 P dimers (FIG. 6). Fitting-in of the crystal structure of the P dimer into the density map of cryo-EM of the small P-particle showed that the orientation of the P dimers is similar to those in the P-particle. In vitro HBGA binding assay revealed that small P-particle has a similar binding profile as NOR VLP and P-particle. Discovery of the small P-particle provides an additional candidate in our P-particle system in case a smaller P-particle is necessary for a specific application.

Figure 7:
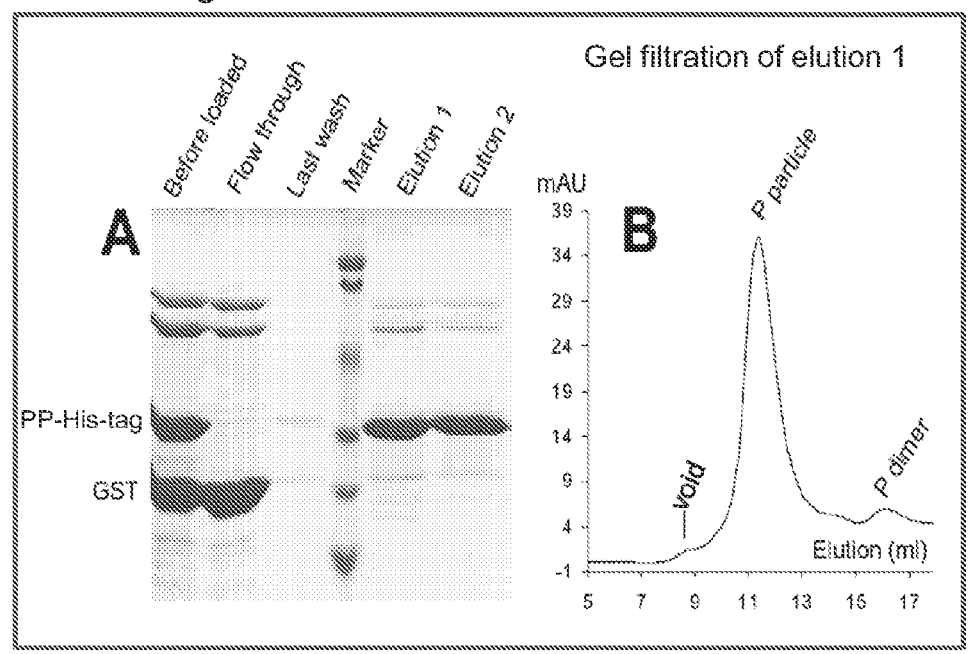
Figure 9:
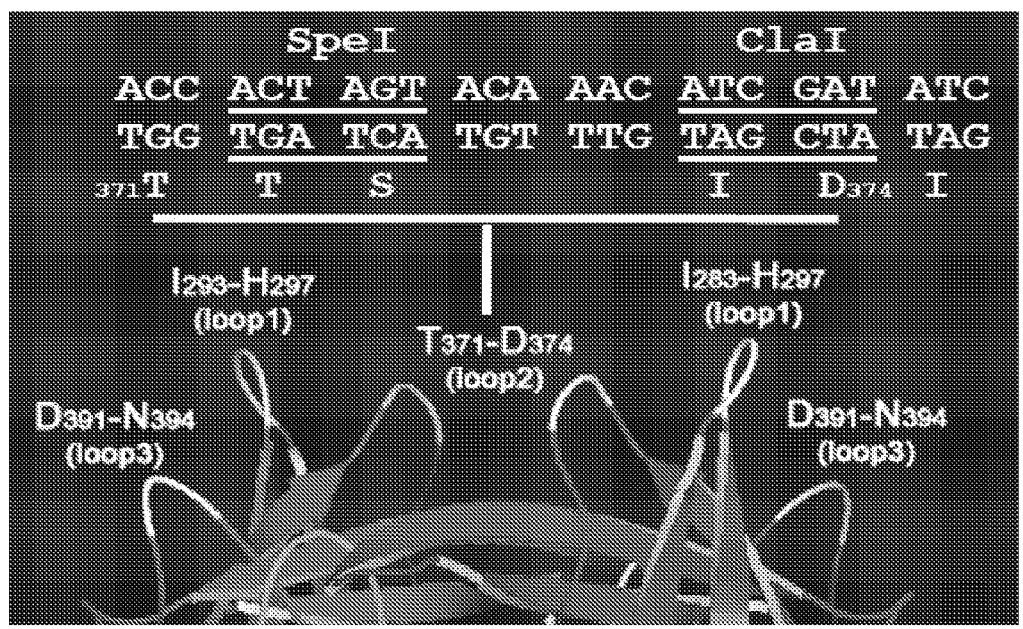
Figure 10:
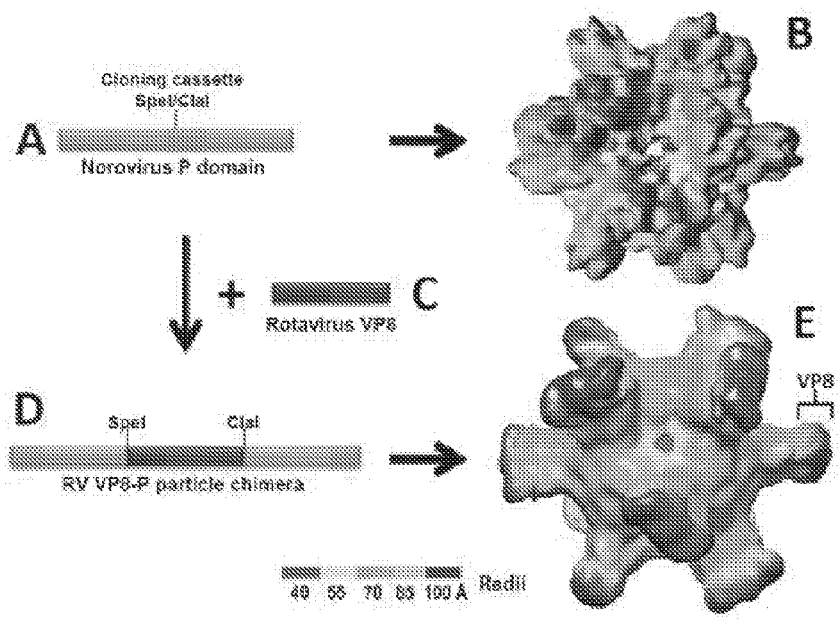

The NOR-based antigen-P-particles of the present invention can be constructed to carry foreign antigens in one or more of the presenting loops of each P-domain dimer or monomer subunit. A wide variety of polypeptide and biological relevant epitopes, including but not limited to the His-tag (7× Histidines), the murine cytomegalovirus (MCMV) T cell epitope (9 amino acids), the *Pseudomonas* epitope Epi8 (14 amino acids), and two RV VP8 core proteins (159 amino acids each) that are RV surface antigen, can be inserted into any one or more of Loop 1 (1293-H297, SEQ ID NO:1), Loop2 (T371-D374, SEQ ID NO:2), or Loop 3 (D391-N394, SEQ ID NO:3), shown in FIG. 9, of the P-particle without affecting the formation and stability of the substituted P-particle. This is demonstrated for Loop 2 by gel-filtration as shown in FIG. 7, panel B and FIG. 8, Panel D. The exposure of the His-tag was shown by its high affinity to talon-resin (FIG. 7, panel A). Exposure of the VP8 has been shown by EIA using antibody against RV VP8 (FIG. 8, Panel E) and by 3D structure reconstruction of the VP8-P-particle chimera using cryo-EM (FIG. 10, Panel E). These data support our hypothesis that the P-particle can be developed into an effective vaccine platform to present diversified foreign antigens.

Figure 8:
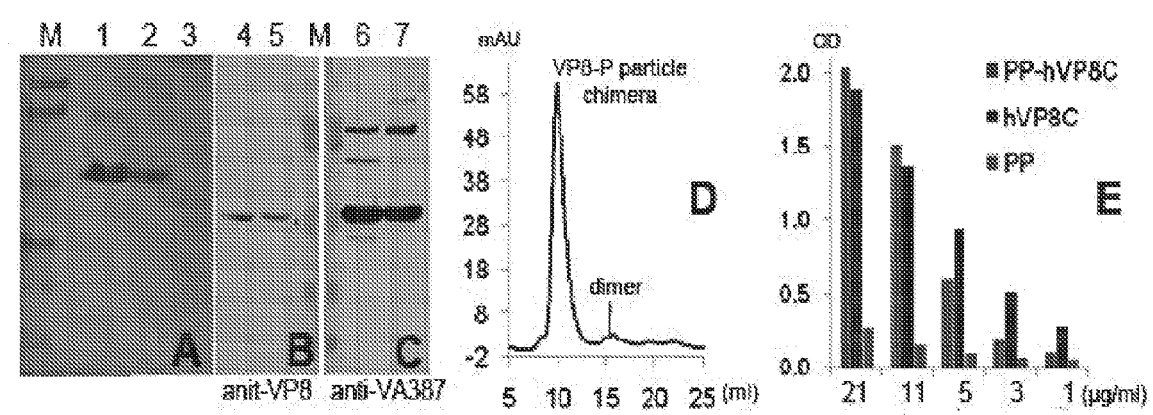

An antigen-P-particle vector can be constructed with a cloning cassette. Based on the crystal structure of the P dimer, a cloning cassette containing restriction sites can be placed into one or more of the loops of the P-particle vector, including onto the tips of the loops. FIG. 9 shows a cloning cassette containing a Spe I site and a Cla I site placed onto the tip of Loop2 of the P-particle vector. This P-particle vector with cloning cassette is employed for the successful insertion of a RV VP8 and GFP onto the surface of the P-particle, as shown in FIGS. 8 and 10.

Examples of restriction sites, including rare and unique restriction sites, and methods of inserting restriction sites into any one or more of the surface loops of the P-domain monomer or P-particle, are well known to persons skilled in the art, and are described in US Patent Publications 2004/0185556 and 2008/0085553 to Reed et al., the disclosures of which are incorporated herein by reference in their entirety. These restriction sites are encoded in the DNA molecule and typically comprise a double-stranded palindromic sequence. For some restriction enzymes, as few as 4-6 nucleotides are sufficient to provide a restriction site, while some restriction enzymes require a restriction site of 8 or more nucleotides. The enzyme EcoR1, for example, recognizes the hexanucleotide sequence: $^{5'}$ G-A-A-T-T-C$^{3'}$, wherein 5' indicates the end of the molecule known by convention as the "upstream" end, and 3' likewise indicates the "downstream" end. The complementary strand of the restriction site would be its anti-parallel strand, $^{3'}$=G-A-A-T-T-C-$^{5}$.

The NOR P-particle can tolerate a large foreign antigen insertion. By way of example only, the green fluorescence protein (GFP, 238 amino acids) has been inserted into Loop2 of the NOR P-particle and the resulting chimeric particles are highly stable as determined by gel filtration analysis. The exposure of the GFP has been shown by EIA using the GFP specific antibody and fluorescence microscope (data not shown).

In an embodiment of a method, a modified NOR P-particle is used to induce antibodies reactive to both NOR and a foreign antigen. In a specific, non-limiting example, a RV VP8-P-particle is used to induced antibodies reactive with both RV and NOR. Mammals immunized with the VP8-P-particle chimera result in levels of antibodies reactive to both NOR P-particle and RV VP8, and can block the binding of NOR VLP to HBGA receptors, and neutralize the replication of RV.

Mouse models of a "neutralization" assay for NORs, and an RV challenge have been developed. NORs remain difficult to be cultivated in cell culture and there is no effective animal model for replication of NORs. To determine the potential protection of an antibody against NOR infection, a HBGA receptor blocking assay has been developed to measure the ability of an antibody in prevention of NORs binding to their host receptors. This assay is based on the saliva or oligosaccharide-based receptor binding assays which is highly sensitive and specific.

An adult mouse model to determine the protective efficacy of a vaccine against RV infection has also been established and used to study RV vaccine development. Mice are immunized with a vaccine candidate and then challenged with a murine RV strain. The amount of fecal shedding of RV antigen in immunized groups is compared to the amount of shedding in control or unimmunized groups as a measure of vaccine efficacy. Immune responses to the vaccine can also be determined by measuring antibody levels and T cell responses.

The present invention also relates to the formation of antigen-P-particles having multiple or multiple-polyvalent presentation of foreign antigens. A modified P-particle vector with two cloning cassettes at two loops (that is, at Loops 1 and 2, Loops 2 and 3, or Loops 1 and 3), can be constructed and evaluated by insertion of a foreign antigen into the two cassettes in a variety of combinations. Non-limiting examples of three combinations include: 1) a His-tag and a Flag-tag (DYKDDDDK, SEQ ID NO:6) in Loops 1 and 2; 2) a His-tag and a VP8 antigen in Loops 1 and 2; and 3) two VP8s in Loops 1 and 2. These embodiments can provide two different small antigens, or one small antigen and one larger antigen, or two larger antigens, presented efficiently on the same substituted P-particle. The chimeric P-particle formation will be determined by gel filtration, while the exposure of the inserted antigens can be examined by EIA using specific antibodies.

A modified P-particle vector with three cloning cassettes at all three loops (Loops 1, 2 and 3) can be constructed and evaluated by insertion of a foreign antigen into the three cassettes in a variety of combinations. A non-limiting example includes: 1) three 7×His-tags; and 2) a 7×His-tag, a myc-tag (EQKLISEEDL, SEQ ID NO:7) and a Flag-tag. The first combination presents the same small epitope multiply onto all three loops of each P-domain monomer of substituted the P-particle, conferring 72 (3×24) copies of the antigen on a P-particle. The second combination provides three different small epitopes presented simultaneously on each of the P-domain monomer subunits, resulting in a trivalent P-particle vaccine for three different antigens.

Figure 13:
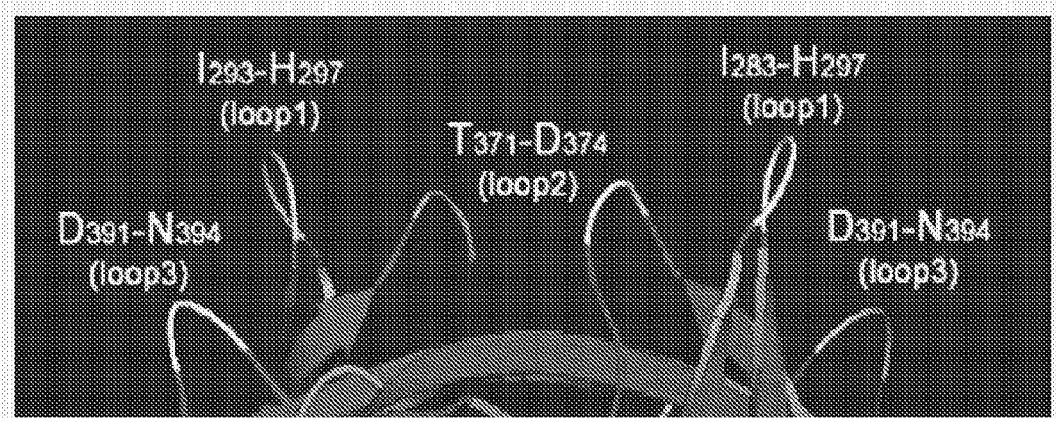

The present invention thus provides a P-particle vector for convenient and diverse antigen insertions. An embodiment of a modified P-particle vector can include three P-domain monomer vectors, each modified P-domain monomer containing a single unique cloning cassette in each of the three surface loops, respectively. Another embodiment of a modified P-particle vector includes a P-domain monomer vector having two cloning cassettes in any one, or any two, of the three loops (for example, in Loops 1 and 2), or all three of the loops. Another embodiment of a modified P-particle vector can have three cloning cassettes in all three loops of each P-domain monomer. The enzyme recognition sites for each cloning cassette, as shown in FIG. 13, may be modified depending on the need for cloning of the DNA sequence of the antigen of interest. These vectors are for single presentation of a single antigen or for multiple presentations of either the same or different antigens. The construction of these P-particle vectors with different cloning cassettes can be achieved by site-directed mutagenesis, as is known in the art.

Mutagenesis and Recombinant DNA Cloning Procedures.

Figure 12:
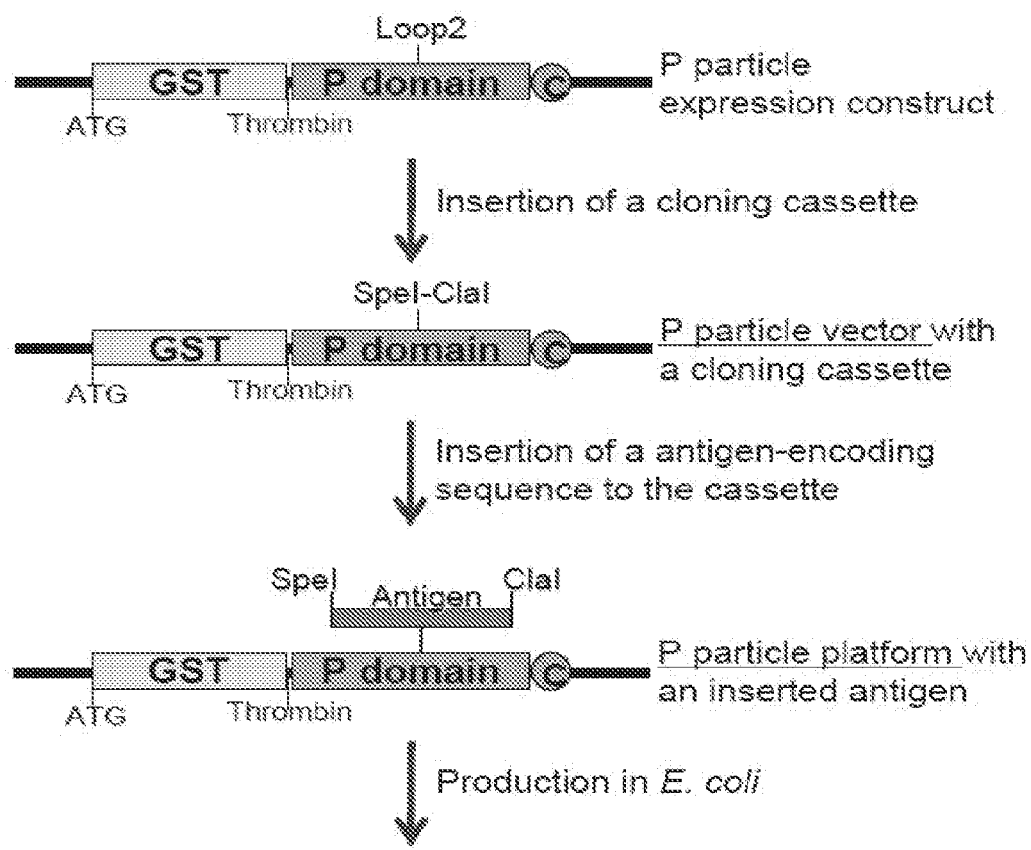

Generation of different modified or substituted P-particle vectors typically starts with a wild type P-particle expression construct as shown in FIG. 12 that contains sequences encoding a P-domain of a NOR (specifically, as an example, the P-domain (SEQ ID NO:12 of NOR strain VA387, SEQ ID NO:11) and a short peptide with cysteines, in a suitable plasmid (specifically, by example, plasmid pGEX-4T-1, available from Amersham Biosciences). The cloning cassettes are introduced at specific sites of the P-domain sequences that encodes the surface loops, as shown in FIG. 13, one-by-one, by site-directed mutagenesis, by well known means, including those described in Tan et al., 2003, "Mutations within the P2 domain of norovirus capsid affect binding to human histo-blood group antigens: evidence for a binding pocket", J Virol 77:12562-71, Tan et al., 2006, "C-terminal arginine cluster is essential for receptor binding of norovirus capsid protein", J Virol 80:7322-31, Tan et al., 2005, "The p domain of norovirus capsid protein forms a subviral particle that binds to histo-blood group antigen receptors", J Virol 79:14017-30, and Tan et al., 2008, "Elucidation of strain-specific interaction of a GII-4 norovirus with HBGA receptors by site-directed mutagenesis study", Virology 379:324-334, the disclosures of which are incorporated herein by reference in their entirety. The positions, compositions and sequences of the three surface loops by crystallographic studies are described in Bu et al., 2008, "Structural basis for the receptor binding specificity of Norwalk virus", J Virol 82:5340-7, and Cao et al., 2007, "Structural basis for the recognition of blood group trisaccharides by norovirus", J Virol 81:5949-57, the disclosures of which are incorporated herein by reference in their entirety.

Based on this structural and sequence information, specific primers can be designed and synthesized with insertion of specific enzyme recognition sites as a cloning cassette in the appropriate position. Typically, two amino acids at the tip (the most exposed position) of the surface loops can be chosen to insert the sequence of the cloning cassette, either by replacing the two amino acids or by inserting the sequences between the two amino acids. The QuikChange Site-Directed Mutagenesis Kit (Stratagene) can be used to introduce the cloning cassettes into the loops, as is well known. The exact position of introduction for a specific antigen may be modified to improve the stability or efficacy of the resulting antigen-P-particle chimera. For insertion of a cloning cassette with longer sequences, stepwise site-directed mutagenesis can be performed for optimal insertion. The resulting plasmids of the substituted P-particle vectors after site-directed mutagenesis can then be amplified through conventional cloning procedures of transformation of the plasmids into E. coli and plasmid DNA preparation using plasmid DNA preparation kit (Qiagen), by well known means. After confirmations of the inserted cloning cassettes by sequencing by well known means, the antigen-P-particle vectors can be tested for their capacity of antigen insertion, stability of chimeric P-particle formation, and efficacy of the antigen presentation as a useful and effective vaccine.

Proper chimeric P-particle formation can be determined to evaluate the capability and efficiency of the P-particle vectors for antigen presentation. After insertion of an antigen or epitope into the P-particle platform (that is, insertion of an antigen or epitope into a P-domain monomer followed by assembly of the P-domain monomers into dimers and then to the antigen-P-particles), each of the resulting chimeric proteins can be analyzed for the formation of the target antigen-P-particle chimera, by a gel-filtration using a size-exclusion column (for example, powered by the Akta fast-performance liquid chromatography (FPLC, HE healthcare)). The correctly-formed target chimeras form a single peak at the expected molecular weights (MW) that is ~24 times the MW of the monomer. For example, a His-tag-P-particle has a MW of 870 kDa; for a VP8-P-particle, a MW of 1240 kDa; and for a GFP-P-particle, a MW of 1450 kDa. Multiple presentations of antigens by P-particle follow this calculation. Formation of the chimeric P-particle with the anticipated MW is an important indication of successful insertion of the antigens. Further evidences of chimeric P-particle formation include the EM observation and 3-D structure reconstruction through cryo-EM (see FIG. 10). A stable formation of a modified antigen-P-particle normally leads to excellent immunogenicity of the antigen, and would be a promising vaccine candidate against the corresponding pathogen.

Figure 11:
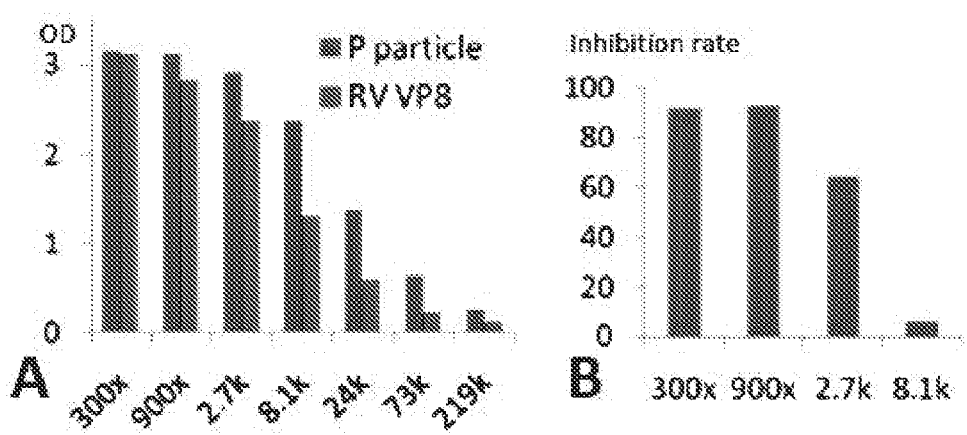

Determination of antigen exposure on the chimeric P-particles is another important indication for the capability and efficiency of the P-particle vectors for antigen presentation. Either or both antibody-specific EIA and Talon resin binding assay can be used for this determination. An antibody-specific EIA is described in Huang et al., "Noroviruses bind to human ABO, Lewis, and secretor histo blood group antigens: identification of 4 distinct strain specific patterns," 2003, J Infect Dis 188:19-31, and Huang et al., "Norovirus and histo-blood group antigens: demonstration of a wide spectrum of 23 strain specificities and classification of two major binding groups among multiple 24 binding patterns," 2005, J Virol 79:6714-22, the disclosures of which are incorporated herein by reference in their entirety, and are illustrated in FIG. 8, Panel E and FIG. 11, Panel A. The purified antigen-P-particle chimera can be coated on a microtiter plate and blocked by non-fat milk. The exposed antigen/epitopes can be detected by the corresponding antibodies. The signal intensity can be recorded by optical density (OD) after inculcation with a secondary antibodies-HRP conjugate and then with HRP substrates. The specific monoclonal antibodies against antigens (for example, His-, Flag- and myc-tag, respectively) are commercially available from Cell Signaling, while the specific antibodies against RV VP8 and NOR P-particle have been made by and are available from the applicants, as shown in FIGS. 8 and 11. For detection of the exposed His-tag another powerful method, the Talon resin binding assay, can be used, in which the Talon resin (Clontech) can bind the His-tag specifically (FIG. 7). Since the resin-bound His-tag-P-particle chimera can be released easily by imidazole (available from Sigma), this assay has been a simple approach for purification of Histag- P-particle chimera from contaminated proteins (see FIG. 7).

EXPERIMENTS

Preparation of Chimeric P-Particles

The previously made RV VP8-P-particle chimera that contains a human VP8 of [P] type 8 strain (FIG. 8, FIG. 10 Panel E) is used. For a chimeric vaccine containing a murine VP8 for the mouse RV challenge studies, the human VP8 is replaced by the murine (EDIM) VP8 in the VP8-P-particle chimera. Both human and mouse RV chimeric P-particles are produced in E. coli using established procedures. Following a partial purification by the GST-affinity columns (Glutathione Sepharose 4 Fast Flow, HE Healthcare), the chimeric P-particles are further purified by a FPLC system (GE Healthcare) using a sized exclusion column. The resulting chimeric P-particle preparations reach a high purity (~95%) and are used as immunogens to immunize mice. As seen in FIG. 8, Panel A of the SDS PAGE shows recombinant RV VP8-P-domain chimera (53.5 kDa) purified by affinity column (lane 1) and further by gel filtration (Panel D) with the P-particle- (lane 2) and the P-domain dimer (lane 3) fraction. In Panels B and C are shown Western analysis of the VP8-P-particle chimera using antibodies against VP8 (Panel B, lanes 4 and 5) or against NOR VLP (Panel C, lanes 6 and 7). In Panel D, gel-filtration of the affinity-purified VP8-P-domain chimera (lane 1) indicates that the vast majority of the protein forms P-particle (~1300 kDa). Panel E shows enzyme immunoassay (EIA) results using antibodies against VP8 to detect coated VP8-P-particle chimera (PP-hVP8C), recombinant VP8 (blue, hVP8C) and P-particle alone (PP, control). Lanes M shows prestained protein markers, in bands from the top of 113, 92, 52, 35, 29 kDa. FIG. 10 shows the production of the RV VP8-P-particle chimera. The P-particle vector with a cloning cassette in the Loop 2 (view A) produces wild type NOR P-particle (view B). When a RV VP8-encoding sequence (view C) is cloned into the P-particle vector (view D), it produces the RV VP8-P-particle chimera (view E) with indication of the RV VP8 at the outermost surface of the chimera.

Immunization of Mice.

Female BALB/c mice at 6 weeks of age (Charles River Labs) are immunized with highly purified RV VP8-P-particle chimera orally or intranasally at different doses with and without an adjuvant [LT (R192G)]. The wild type P-particles are included as a control. For intranasal route of vaccination, three initial dosages (5, 15, and 45 μg/mouse, three doses) of the wild type P-particles and the VP8-P-particle chimera in a volume of 50 μl are administrated (25 μl per nostril). For oral route a total of 200 μl of the same amount of vaccine are delivered directly by an intragastric cannula into the stomach using a 20-gauge stainless steel feeding needle attached to a 1-ml syringe. The animals (12 mice/group) are monitored for general appearance and weight loss to evaluate the possible adverse effects of the vaccines. Pre- and convalescent serum samples are collected and tested for antibody responses to NOR and RV by EIAs using recombinant NOR VLP and RV VP8 as antigens. Stool samples are collected for secretory IgA against to NOR and RV. A group of mice (N=5) are immunized with bacteria-expressed glutathione S-transferase (GST) as negative control.

Assessment of Immune Responses by in Vitro Assays.

Mouse sera, pre- and post-immunization of the vaccines via different administration regimes, are collected and their specific antibodies titers against NOR and RV are determined using the type-specific antibody detection EIAs, as described in Huang et al., 2003, J Infect Dis 188:19-31, and Huang et al., 2005, J Virol 79:6714-22, supra. Secretory IgA in the stool samples are examined for response to NOR and RV as an indication of mucosal immunity. For RVs, a neutralization assay is performed on the serum samples for inhibition of RV replication in cell cultures. For NORs, NOR-receptor blocking assays are performed to measure the inhibition of NOR VLP binding to their HBGA receptors by the antibodies as a potential "neutralization" activity.

The homologous antibody responses against the same VA387 VLPs or P-particles are used since VA387 represents the dominant GII-4 genotype that is responsible for 65-85% of NOR-associated gastroenteritis worldwide. The in vitro blocking assay of NOR-receptor binding is used to evaluate the potential neutralization of antibody on NORs. The mouse sera from different administration regimes of the VP8-P-particle vaccine are examined for their blocking effects on NOR VLPs binding to their HBGA receptors. Again, the blocking effect of the antibodies is examined on the binding of homologous strain VA387 VLP to their HBGAs (A, B, H, Lewis B, and Lewis Y antigens). Briefly, the well-characterized saliva with known HBGAs or synthetic oligosaccharides is coated on a microtiter plate. After blocking by non-fat milk, NOR VLP that has been incubated with the antibody for 30 minutes is added to the plate. The bound VLP to HBGA receptors are detected by guinea pig hyperimmune serum against specific VA387 VLP, followed by the addition of HRP-conjugated goat anti-guinea pig IgG (ICN, Aurora, Ohio). The signal intensity (optical density, OD) is read by an ELISA plate reader at 450 nm wavelength. The blocking effects will be determined by a comparison between the bindings with and without antibody treatment.

The neutralization assays using cell culture to measure plaque reduction are performed to examine the antibodies induced against the VP8-P-particle chimera in the mice. The cross neutralization of the [P] type of the VP8-P-particle chimera to other RV types are tested using different RV strains that are available in the inventor's laboratory. Tissue culture-adapted Wa strain, murine RV EDIM strain, and the MA104 green monkey kidney cell line are used. Briefly, MA104 cells are cultivated in a 6-well plate and RV titer for formation of ~50 plaques/well are determined by serial dilution of RV inoculums. For the assay, RV are incubated with sera at specific dilutions for 60 min, the mixture is added to the cells (MA104) in the 6-well plate. After 2 hour the plates are washed and then overlayed with media containing 0.8% agarose. After 4-5 day incubation at 37° C., the numbers of plaques in each well are counted. The reduction in plaque numbers in the wells containing sera as compared to untreated wells determines the amount of neutralizing antibody present in the sera.

Murine RV Challenge Model.

The procedures of this RV challenge model are described in Choi et al., "Functional mapping of protective domains and epitopes in the rotavirus VP6 protein," 2000, J Virol 74:11574-80; Choi et al., "Functional mapping of protective epitopes within the rotavirus VP6 protein in mice belonging to different haplotypes," 2003, Vaccine 21:761-7; and McNeal et al., 1999, J Virol 73:7565-73.41, the disclosures of which are incorporated herein by reference in their entirety, to examine the protection efficacy of the vaccine. RV antibody-free BALB/c mice at age of 6 weeks (Harlan-Sprague-Dawley, Indianapolis, Ind.) are immunized orally or intranasally by the VP8-P-particle chimera vaccines. Two to four weeks after the last immunization, mice are orally (via gavage, generally carried out by passing a feeding tube through the nose or mouth into the esophagus) challenged with murine RV EDIM strain at a dose of 4×10⁴ FFU (focus-forming units), which is equivalent to 100 50% shedding doses. To determine RV antigen in stools, two fecal pellets are collected from each mouse for 7 or more days following EDIM challenge and kept in 1 ml of Earle's balanced salt solution. Samples are stored frozen until analyzed, at which time they will be homogenized and centrifuged to remove debris. Quantities of RV antigen in the fecal samples are determined by ELISA as described previously.

Results.

The results show that the VP8-P-particle induces RV- and NOR-specific antibodies in the treated mice, and the antibodies block the binding of NOR VLP to its HBGA receptors, neutralize the replication of RV in cell culture, and provide immune protection in the mouse challenge model. The VP8-P-particle vaccines exhibit no cytotoxicity or side effects.

Expression Constructs.

The P particle expression vector of pGEX-4T-1 [Glutathione S-Transferase (GST) Gene fusion System, GE Healthcare life sciences] containing the VA387 norovirus (GII.4) P domain (SEQ. ID. NO:12)-encoding sequence and a cysteine-containing peptide was used as the template for construction of various chimeric P particles. For making the P particle-His-tag chimera, the His-tag-encoding sequence was inserted into the sequence that encodes loop 2 between N372 and D374 (FIG. 7 and FIG. 14A) through site-directed mutagenesis (see below). For the chimeric P particles containing human rotavirus VP8 antigens, a cloning cassette with enzyme sites of SpeI and ClaI/EcoRI was first introduced into loop 2 to replace the sequence from T369 to D374 (FIG. 16A) by site-directed mutagenesis. The VP8 antigen cDNA sequences of a [P]8 strain (Wa, L65-L223, GenBank accession: VPXRWA) and a [P]4 strain (DS1, L65-1223, GenBank accession: VPXRDS) were cloned into the cassette. For cloning the cDNA sequence of murine rotavirus (EDIM) VP8 antigen (L65-L222, GenBank accession: AF039219) to the P particle, another cloning cassette with XbaI and Bgl II sites was inserted between N372 and N373. For making the P dimer-His-tag chimera, the His-tag was linked to the N-terminus of the P domain with the hinge. For making the chimeric maltose binding protein (MBP) containing peptide CNGRC (SEQ. ID. NO:4) or CDCRGDCFC (SEQ. ID. NO:5), the peptide was fused to the N-terminus of the MBP in the vector of pGEX-4T-1. The expression construct of the His-tagged *Thermotoga maritima* α-L-Fucosidase (GenBank accession: TM0306) in the pDEST17 (Gateway, Invitrogen) (29) was kindly provided by Drs. Henrissat and Bourne (Architecture et Fonction des Macromole'cules Biologiques, UMR 6098, CNRS, and Universite's Aix-Marseille I and II, 31 Chemin J. Aiguier, F-13402 Marseille, Cedex 20, France).

Expression and Purification of Recombinant Proteins.

Recombinant proteins were expressed in *E. coli* (BL21) with an induction of 0.25 mM isopropyl-β-D-thiogalactopyranoside (IPTG) at room temperature (~25° C.) overnight as described elsewhere. Purification of the recombinant GST-fusion proteins was carried out using resin of Glutathione Sepharose 4 Fast Flow (GE Healthcare life Sciences) according to the manufacturer's instructions. GST was removed from the target proteins by thrombin (GE Healthcare life Sciences) cleavage either on bead or in solution (phosphate buffer saline, PBS, pH7.4) followed by further purification through gel filtration chromatography. Purification of the His-tagged proteins was conducted using TALON His-Tag Purification Resins (Clontech, Mountain View, Calif.) according to the manufacturer's instructions. The His-tagged proteins were eluted from the resin by PBS containing 250 mM imidazole (Sigma-Aldrich, St. Louis, Mo.). Further purification of the resin-purified proteins was performed through gel filtration chromatography.

Gel Filtration Chromatography was carried out through an AKTA FPLC System (GE Healthcare life Sciences) as described previously. Briefly, the affinity column-purified proteins were loaded on a size exclusion column Superdex 200 (GE Healthcare life Sciences) powered by an AKTA FPLC system (model 920, GE Healthcare life Sciences). The molecular weights of the eluted fractions were calibrated by Gel Filtration Calibration Kits (GE Healthcare life Sciences). Alternatively, the peaks of void volume, the chimeric P particle, and the P dimer can be determined by blue dextran 2000 (~2000 kDa, GE Healthcare life Sciences), the wild type P particle (830 kDa) and wild type P dimer (69 kDa) of norovirus VA387 (GII.4), respectively. The proteins of interested fractions were further analyzed by sodium dodecyl sulfate polyacrylamide gel electrophoresis (SDS PAGE) and/or Western blot analysis.

SDS PAGE and Western Blot Analysis.

Recombinant proteins were analyzed by SDS PAGE using a 10% gel. The specific compositions of recombinant proteins were detected by a Western blot analysis as described elsewhere using hyperimmune sera against norovirus VLP (VA387, GII.4, 1:3000) or rotavirus VP8 antigen (Wa, 1:3000). Blotted membrane was blocked by 5% nonfat milk. Secondary antibody-HRP (horseradish peroxidase) conjugates (1:5,000, ICN Pharmaceuticals, Costa Mesa, Calif.) were used and the HRP was detected by ECL Eastern Blotting Detection Reagents (GE Healthcare life Sciences, Buckinghamshire, England). The ECL signals were captured by Hyperfilm ECL (GE Healthcare life Sciences, Buckinghamshire, England).

Site-directed Mutagenesis was performed to insert His-tag and construct cloning cassettes into loop 2 of the norovirus P domain following the procedure of the QuikChange Site-Directed Mutagenesis Kit (Stratagene, La Jolla, Calif.) provided by the manufacturer as described previously. A primer pair: caccactgacacaaaccaccaccaccatcatcaccacgatcttcaaactggcc/ggccagtttgaagatcgtggtgatgatggtggtggt ggtttgt gtcagtggtg (SEQ. ID. NO:8), was used for the insertion of a string of 7 histidines into loop 2 between N372 and D374 (FIG. 7 and FIG. 14A). In addition, a cloning cassette with three enzyme sites (Spe I and Cla I/EcoRI) in loop 2 of the norovirus P domain was constructed using primer pair gttcaatacaccactagtacaaacatcgatatccttcaaactggc/gccagtttgaaggatatcgatgtttg-tactagtggtgtattgaac (SEQ. ID. NO:9), to facilitate the insertion of the coding sequences of human rotavirus VP8 antigens. Another cloning cassette with XbaI and Bgl II sites was made using another primer pair tacaccactgacavaaa ctc tagacacagatctaatgatcttcaaactgg/ccagtttgaagatcattagatctgt-gtctagagtttgt gtcagtggtgta (SEQ. ID. NO:10), to help insertion of the coding sequence of murine rotavirus VP8 antigens.

Cryo-Electron Microscopy (cryo-EM) Techniques.

Cryo-EM Image Collection.

The procedure used for structure reconstruction of the wild type P particle described in our previous studies was adapted here. Briefly, aliquots (3-4 μl) of the purified P particle-VP8 (Wa) chimera were flash frozen onto Quantifoil grids in liquid ethane cooled by liquid $N_2$. The sample grids were loaded into the microscope and low dose images (~20 $e/A^2$) were recorded on films using CM200 cryo-microscope with a field emission gun operating at 200 KV. The images were taken at nominal magnification of ×50,000 and in the defocus range of 2.0 to 4.0 μm. The micrographs were selected and digitized using a Nikon Super CoolScan 9000ED scanner at step size of 6.35 μm/pixel. The scanned images were binned resulting in the final sampling of the images at 2.49 Å/pixel for further image processing and 3-D reconstruction.

Cryo-EM Image Processing and 3-D Reconstruction.

The images of the chimeric P particles were selected using EMAN's boxer program. The selected images were manually filtered to exclude false positive. The EMAN's ctfit program was used to manually determine the contrast-transfer-function (CTF) parameters associated with the set of particle images originating from the same micrograph. Initial model of the chimeric P particles were created using EMAN's startoct program. Then the EMAN's refine program was used to iteratively determine the center and orientation of the raw chimeric particles and reconstruct the 3-D maps from the 2-D images by the EMAN make3d program until convergence. Octahedron symmetry was imposed during reconstruction of the chimeric P particles.

Cryo EM Model Evaluation and Analysis.

The crystal structure of rotavirus VP8 antigen (Wa, 2DWr, L65-L223) was fitted into the extended protrusions of the 3D structure of the P particle-VP8 (Wa) chimera using UCSF Chimera software. Simple rigid body motion was considered to find the best matching of the x-ray structure to the 3D structure of chimeric P particles.

Enzyme Immune Assay (EIA)

was used to measure immune reactivity and antibody titers of mouse antisera that were induced by P particle-antigen chimeras. Different antigens were used for variable antisera: the His-tagged *T. maritima* α-L-Fucosidase for sera induced by the P particle-His-tag chimera, MPB-CNGRC and MPB- CDCRGDCFC for sera induced by the P particle containing unexposed peptide CNGRC (SEQ. ID. NO:4) or CDCRGD-CFC (SEQ. ID. NO:5), free VP8 for sera induced by the P particle-VP8 chimera, and GST for sera induced by the P particle-VP8 chimera with GST as internal control. Antigen was coated on a 96-well microtiter plate (Dynex Immulon; Dynatech, Franklin, Mass.). After blocking with 5% nonfat milk, sera at indicated dilutions were incubated with the coated antigens. The bound antibody was detected by the secondary antibodies-HRP conjugate as described elsewhere. Antibody titers against antigens were defined as the endpoint dilution with a cut off signal intensity of 0.15. Sera from animals that were immunized by wild type P particle or PBS were used as negative controls.

HBGA Binding and Blocking Assays.

The saliva-based binding assays were carried out basically as described elsewhere. Briefly, boiled saliva samples with known HBGA phenotypes were diluted 1000 fold and coated on 96-well microtiter plates (Dynex Immulon; Dynatech, Franklin, Mass.). After blocking with 5% nonfat milk, VLPs or P particles of norovirus (VA387, GII.4) were added. The bound VLPs/P particles were detected using our home-made rabbit anti-VA387 VLP antiserum (1:3,300), followed by the addition of HRP-conjugated goat anti-rabbit IgG (ICN, Pharmaceuticals, Costa Mesa, Calif.). The blocking effects of the mouse sera induced by the P particle-VP8 chimera on the norovirus VLP-saliva binding were measured by a pre-incubation of VLP with diluted serum for 30 min before the VLP was added to the coated saliva. The blocking rates were calculated by comparing the ODs measured with and without blocking with the mouse sera from immunized animals. The blocking rates of the sera from free VP8 immunized animals were used as negative controls.

Immunizing Mice for Antibody Responses.

Female BALB/c mice at 6 weeks of age (Harlan-Sprague-Dawley, Indianapolis, Ind.) were immunized with purified chimeric P particles or free antigens at a dose 5-15 µg/mouse three to four times in a two-week interval. For comparison of immune responses to the P particle- or P dimer-presented His-tag, 5 µg/mouse of recombinant P particle-His tag chimera, and P dimer-His tag or wild type P particles were administered to mice (n=5). For comparison of the immune responses to the unexposed peptides, 5 µg/mouse of recombinant P particles containing either unexposed peptide CNGRC (SEQ. ID. NO:4) or CDCRGDCFC (SEQ. ID. NO:5) were administered to mice. The immunogens were given four times subcutaneously with the Freund's adjuvant. For comparison of the immune responses to P particle-presented VP8 and free VP8, 5 µg/mouse of free VP8 and 15 µg/mouse of P particle-VP8 chimera, in which both immunogens are in the same molar amounts of VP8, were administered to mice either intranasally without an adjuvant or subcutaneously with Freund's adjuvant (n=5-7) for three doses. Equal molar amount of GST were added to the immunogen as internal control. Immunization of P the particle-VP8 vaccine to mice for protection was described below. Blood was collected by puncture of retro-orbital capillary plexus before immunization and two weeks after the final immunization. Sera were processed from blood after overnight stay at 4° C. followed by centrifugation.

Rotavirus Plaque Assay was performed to determine neutralization of antisera induced by chimeric P particle containing rotavirus VP8 antigen on rotavirus replication in cell culture. Tissue culture-adapted rotavirus Wa strain grown in MA104 monkey kidney cells were used in this assay. The MA104 cells were cultivated in 6-well plates and a rotavirus titer of ~50 plaques/well was used as the inoculum. For the assay, rotavirus was incubated with mouse sera at given dilutions for 60 min. The mixture was then added to the MA104 cells in the 6-well plate. After 2 hours the plates were washed and then overlaid with media containing 5 µg/ml trypsin (Invitrogen, Carlsbad, Calif.) and 0.8% agarose. After 4-5 day incubation at 37° C., the numbers of plaques in each well were counted. The amount of neutralizing antibody in the sera was determined by the reduction in plaque numbers in the wells treated with antisera comparing with that of untreated control wells.

Murine Rotavirus Challenge Model.

The rotavirus challenge model described in previous studies was followed to examine the protection efficacy of the P particle-VP8 vaccine. Rotavirus antibody-free BALB/c mice (n=5-7) at 6 week of age (Harlan-Sprague-Dawley, Indianapolis, Ind.) were immunized intranasally three times with the chimeric P particle (15 µg/mouse) containing murine rotavirus (EDIM) VP8 antigen without an adjuvant. Free murine rotavirus VP8 antigen (5 µg/mouse) and the chimeric P particle (15 µg/mouse) containing human rotavirus (Wa) VP8 antigen were included for comparison. In addition, the wild type P particle (vector control) and PBS were administered as negative controls. Two weeks after the last immunization, mice were challenged by oral gavage with murine rotavirus EDIM strain at a dose of $4 \times 10^4$ FFU (focus-forming units), which is equivalent to $10^5$ 50% shedding doses. To measure rotavirus shedding in stools, two fecal pellets were collected from each mouse each day for 6 days following EDIM challenge and kept in 1 ml of Earle's balanced salt solution (EBSS). Samples were stored frozen until analyzed, at which time they were homogenized and centrifuged to remove debris. Quantities of rotavirus antigen in the fecal samples (µg/ml) were determined by ELISA as described previously.

Statistic Analysis.

Graphs were made using GraphPad Prism version 5.00 for Windows (GraphPad Software, San Diego Calif.) and Microsoft Office Excel 2007. The P values were determined by t-test among data groups using GraphPad Prism version 5.00 for Windows.

Results

Production of Chimeric P Particle Containing a His-tag.

Figure 14:
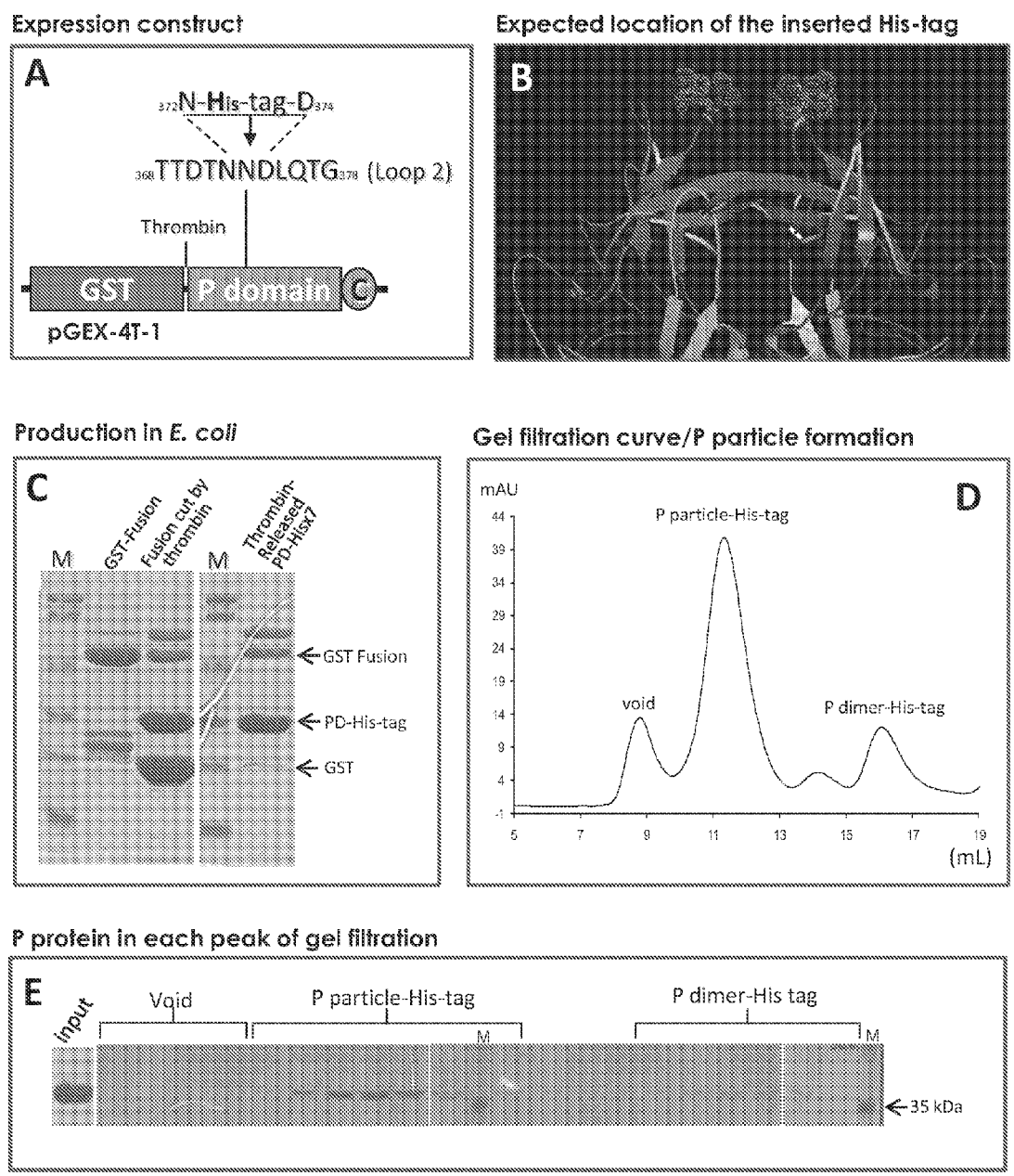

Our study was initiated with an insertion of a small epitope, the poly-histidine (His) tag, into loop 2 of the P particle (FIGS. 3 and 14). Expression and purification of this chimeric P protein in *E. coli* using a GST-gene fusion system resulted in a high yield (>10 mg/liter culture) of the protein with an expected size (~35 kDa) following a digestion of the protein to remove the GST tag (~27 kDa) by thrombin (FIG. 14C). The formation of the chimeric P protein into P particles was shown by a gel-filtration chromatography followed by SDS PAGE and Western blot analysis, in which the chimeric P particle formed the major peak at ~840 kDa (FIGS. 14D and E, data not shown). Exposure of the inserted His-tag on the chimeric P particle was shown by its specific binding to the Talon resin followed by an elution with 250 mM imidazole (FIG. 7A, elution 1 and 2), which resulted in a highly pure prep of the chimeric P particle. Thus, the P particles-His-tag chimera can also be purified from *E. Coli* using the affinity Talon resin (data not shown).

Immune Enhancement of the His-tag by the P Particle Carrier.

Figure 15:
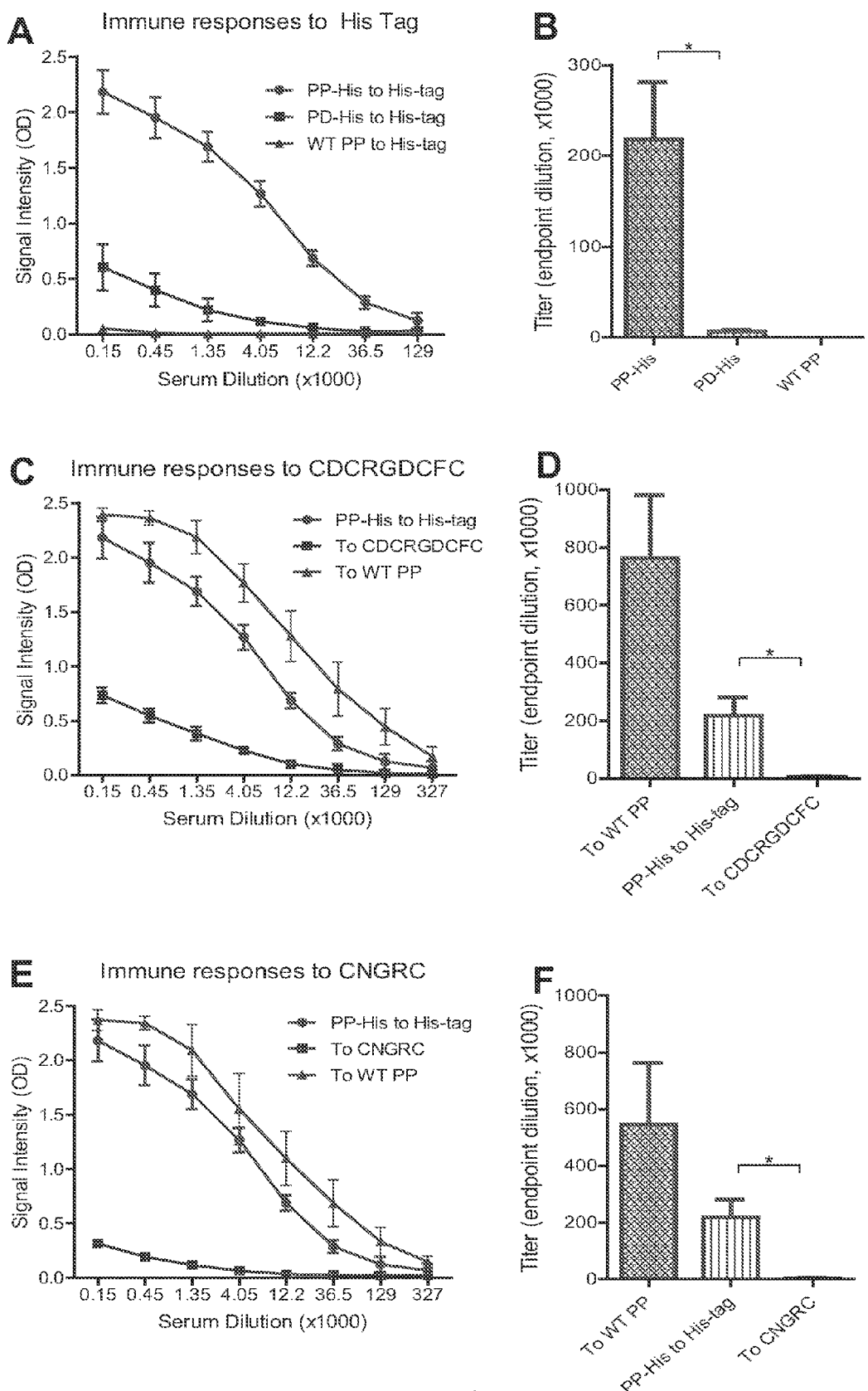

This was determined by examination of immune responses to the His-tag in mice (n=5) following immunization with the P particle-His tag chimera. A significantly higher antibody titer to His-tag was detected in the mice immunized with the P particle-presented His-tag than the P dimer-presented His-tag (P<0.05, FIGS. 15A and B). Two short peptides fused to the N- (CNGRC, (SEQ. ID. NO:4) or C- (CDCRGDCFC, (SEQ. ID. NO:5) terminus of the P domain induced significantly weaker immune responses comparing to that induced by P particle-resented His-tag (FIG. 15C to F). These two peptides have been shown to be buried inside the P particle, indicating a proper exposure of an inserted antigen on the surfaces of the P particles was important for immune enhancement. As expected, all sera reacted strongly to the norovirus P particle platform (FIG. 15 and data not shown).

Development of a Chimeric P Particle Containing the Rotavirus VP8 Antigen.

Figure 16:
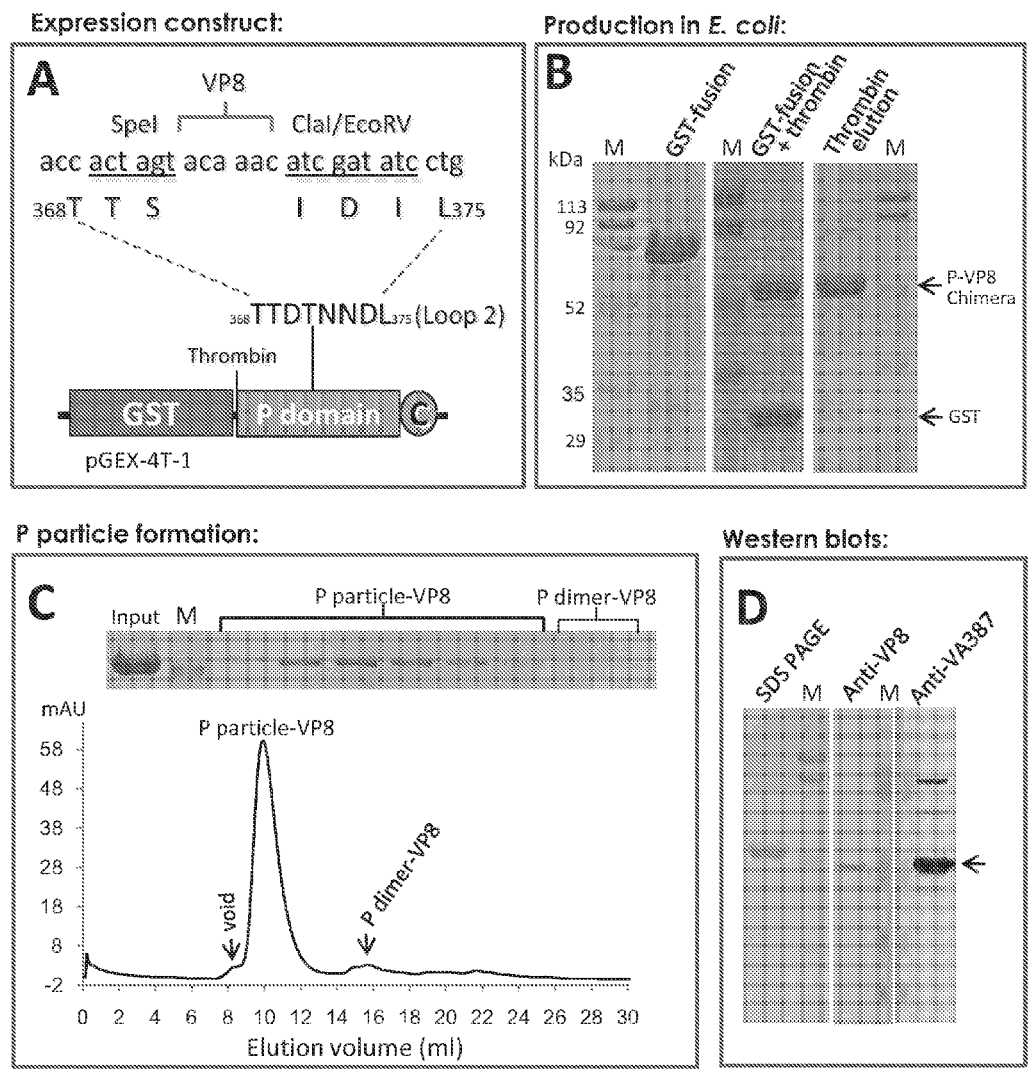

We next examined the capacity of the P particle platform to accommodate a larger polypeptide by the insertion of the rotavirus (Wa) VP8 antigen that contains 159 amino acids. A cloning cassette with three enzyme sites (Spe I and Cla I/EcoRI) in loop 2 of the P particle was constructed (FIG. 16A) to facilitate the VP8 insertion. Expression of the construct in $E.\ coli$ resulted in a high yield (>15 mg/liter culture) of the GST-P-VP8 fusion protein (~78 kDa, FIG. 16B, left panel). Released P-VP8 chimera (~52 kDa) was obtained by thrombin digestion of the GST fusion protein either in solution or on the purification beads (FIG. 16B, middle and right panels, respectively). High rate (>95%) of P particle formation of the P-VP8 chimeric protein was demonstrated by gel-filtration chromatography (FIG. 16C). Western blot analysis showed that the P-VP8 chimeric protein reacted with antibodies against both norovirus VLP (VA387) and rotavirus (Wa) VP8 (FIG. 16D).

Cryo-EM and 3-dimentional image reconstruction showed that the P particle-VP8 chimera remains an octahedral symmetry like the wild type P particle but the chimeric P particle is notably larger (FIGS. 1A and B). The extended protrusion is likely the inserted VP8 that can be recognized by a nick as the potential boundary from the P dimer. Fitting of the crystal structure of rotavirus VP8 antigen of the same Wa strain (2) in the density map of the extended protrusions of the chimera confirmed that the extended protrusion is indeed the VP8 (FIG. 1C to E).

The P Particle Enhanced Immune Responses to VP8.

Figure 17:
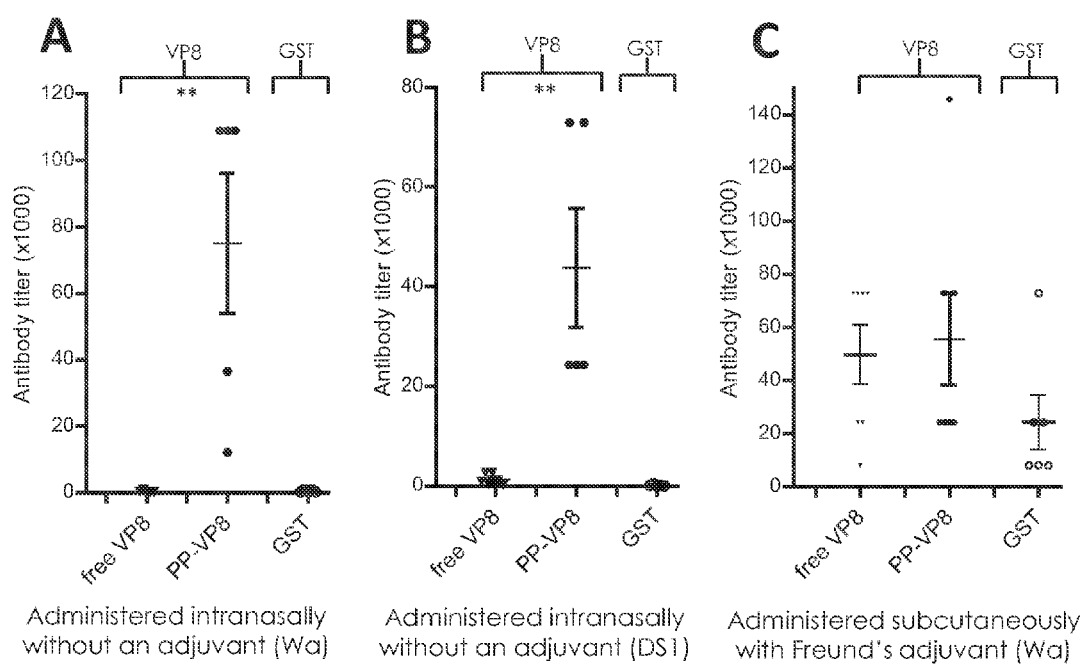

We then studied the immune responses to the P particle presented VP8 antigen in mice. Following immunization with equal molar amounts of the P particle-VP8 chimera and free VP8, the resulting mouse sera were examined by EIA using free VP8 as antigen. The antibody titer against the P particle presented VP8 was significantly higher than that against the free VP8 following an intranasal immunization without an adjuvant (P<0.005). Comparable results were observed for two chimeric P particles containing a VP8 antigen of rotaviruses Wa and DS-1, respectively, comparing to their free VP8 counterparts (FIGS. 17A and B). Only marginal antibody titer against free GST was detected in these animals, further confirming the specific immune enhancement to the P particle presented VP8s. The immune responses of mice following a subcutaneous immunization of above antigens with the Freund's adjuvant were also studied and less difference of antibody titers to VP8 between the free- and P particle presented-VP8 were observed (FIG. 17C).

The P Particle-VP8 Chimera Induced Neutralizing Antibodies Against Rotaviruses.

Figure 18:
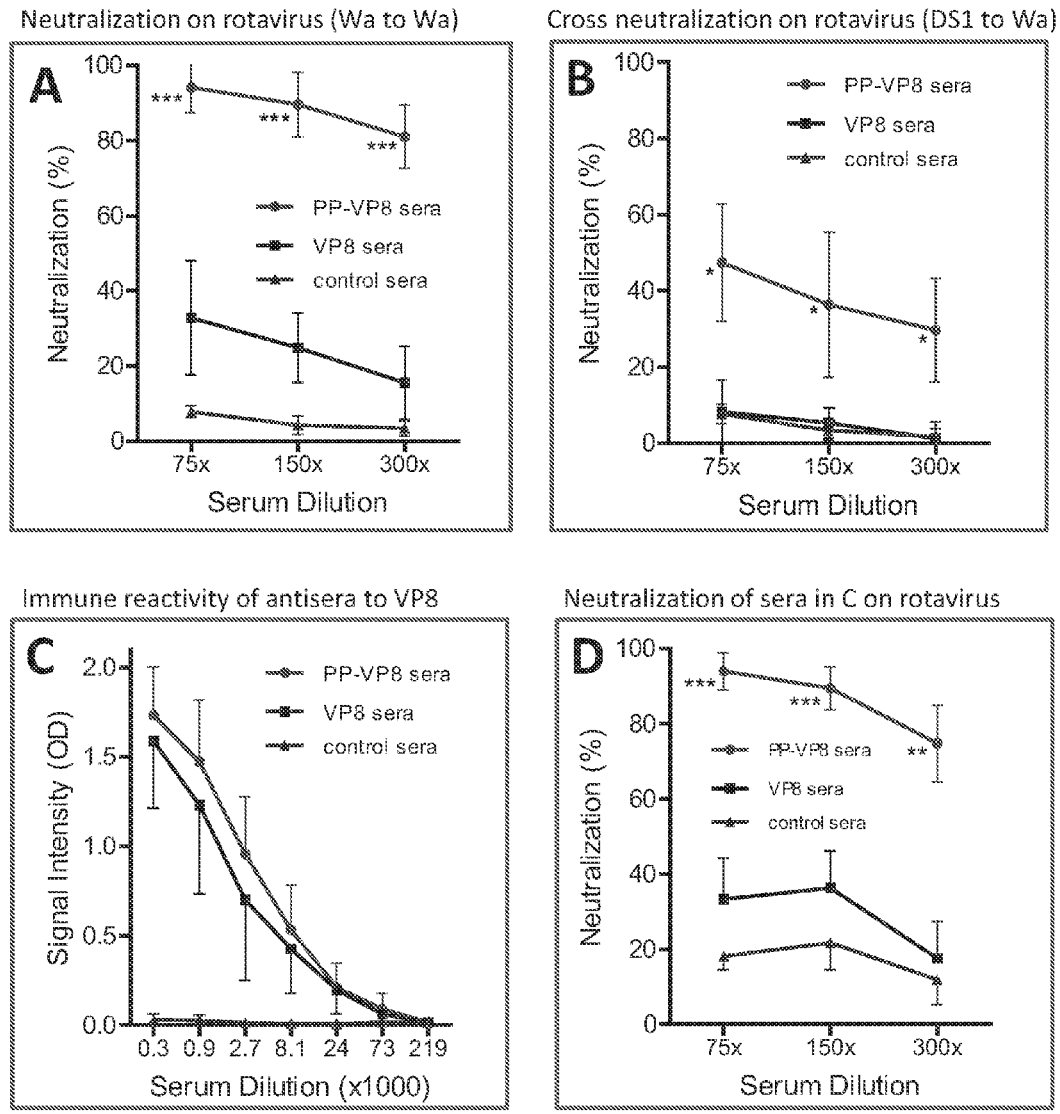

The hyperimmune antisera induced by the P particle-VP8 (Wa, [P]8) chimera through an intranasal immunization (FIG. 17A) strongly reduced the homologous rotavirus (Wa) replication in cell culture. This neutralization titer was significantly higher than the neutralization titer induced by immunization with the free VP8 (P<0.0002) (FIG. 18A). A low level of cross-neutralization after immunization with P particle-VP8 (DS-1, [P]4) chimera to Wa was also observed (P<0.05, FIG. 18B). In contrast, sera from animals immunized with the free VP8 of DS-1 did not show such cross neutralization. In addition, the neutralization titers using sera from subcutaneously immunized animals with the Freund's adjuvant were also measured. To our surprise, among 4 pairs mouse sera with similar immune reactivities to free VP8 antigen in EIAs (FIG. 18C), all sera from animals immunized with P particle-VP8 (Wa) showed significantly higher neutralization titers than that of sera from mice immunized with free VP8 of the same Wa strain (P<0.005, FIG. 18D). These data indicated that the VP8 on the chimeric P particle might be better presented and maintained a proper conformation that is required for a neutralization epitope.

Vaccination with the P Particle-VP8 Chimera Caused Reduced Shedding After Challenge with a Murine Rotavirus.

Figure 19:
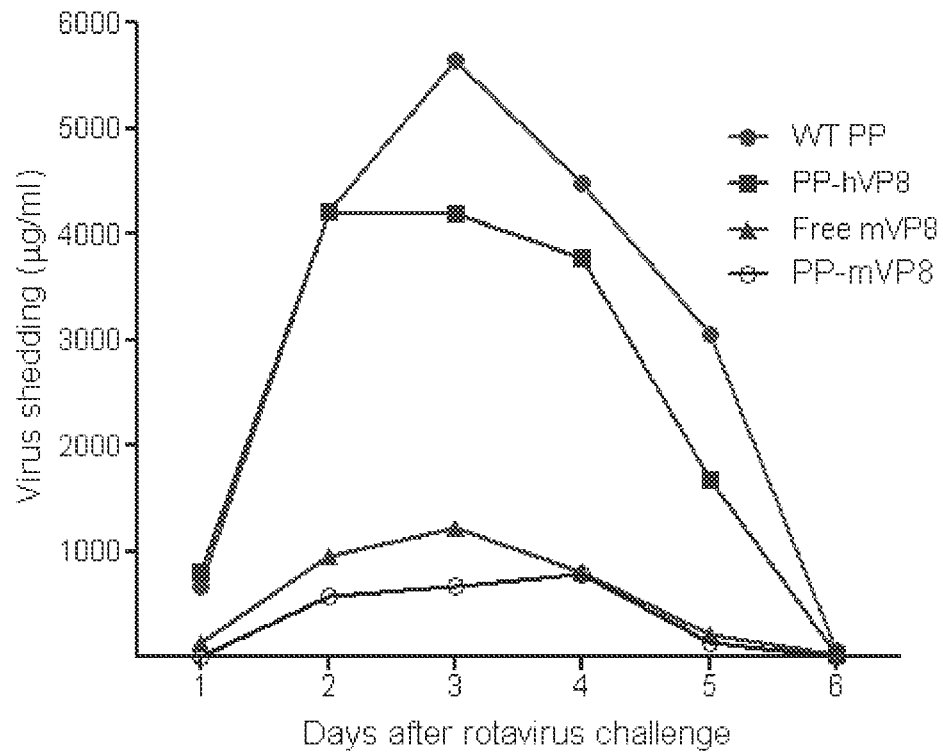

We next examined whether a P particle-VP8 chimeric vaccine could provide protection in vivo using a murine rotavirus model (EDIM strain). To this end, a chimeric P particle containing the EDIM VP8 antigen was constructed and administered to mice (N=5-7) as described in the Materials and Methods. Animals that were immunized with same molar amount of free EDIM VP8, chimeric P particle with human VP8 (Wa), or wild type P particle were included as controls. Two weeks after the last immunization, the animals were challenged with murine EDIM rotavirus. Stool samples were collected for 6 days after challenge and shedding was detected by EIA (Table 1, FIG. 19). Mice vaccinated with the P particle-VP8 (EDIM) chimera shed the lowest quantity of viral antigen. The reduction in shedding was 89% during the six days (P<0.05). There was a 99.2% reduction on day 1 after challenge with EDIM. Mice immunized with free murine VP8 had the next lowest quantity of shedding with an average protection of 77% (P<0.05, day 2 to 5). Immunization with the chimeric P particle vaccine containing a human rotavirus (Wa) VP8 had a small effect on shedding with a 23% reduction suggesting some cross-protection against EDIM. On day 6 in this group, there was significant reduction of shedding (63%, P<0.05).

TABLE 1

Quantity of rotavirus shedding in stools of vaccinated mice after challenge with murine rotavirus strain (EDIM)[1]

| | Days after virus challenge | | | | | | % Reduction in Shedding[3] |
|---|---|---|---|---|---|---|---|
| | 1 | 2 | 3 | 4 | 5 | 6 | |
| WT P particle (N = 7) | | | | | | | |
| Mean antigen shedding[2] | 692.8 | 4215.2 | 5639.9 | 4474.2 | 3045.7 | 64.4 | |

TABLE 1-continued

Quantity of rotavirus shedding in stools of vaccinated mice after challenge with murine rotavirus strain (EDIM)[1]

| | Days after virus challenge | | | | | | % Reduction in Shedding[3] |
|---|---|---|---|---|---|---|---|
| | 1 | 2 | 3 | 4 | 5 | 6 | |
| Standard deviation | 869.9 | 2715.9 | 2932.7 | 2063.1 | 2072.1 | 30.1 | |
| P particle-VP8 Wa (N = 5) | | | | | | | |
| Mean antigen shedding | 801.4 | 4205.1 | 4198.7 | 3768.2 | 1673.1 | 23.8 | |
| Standard deviation | 254.1 | 1644.0 | 1500.6 | 1205.0 | 758.3 | 6.8 | |
| % Reduction in Shedding[3] | −11.2 | 0.2 | 25.6 | 15.8 | 45.1 | 63.0 | 23.1 |
| P value[4] | 0.903 | 0.993 | 0.341 | 0.511 | 0.192 | 0.015* | 0.101 |
| Free VP8 (EDIM, N = 5) | | | | | | | |
| Mean antigen shedding | 143.9 | 949.1 | 1227.0 | 809.8 | 211.8 | 29.6 | |
| Standard deviation | 151.8 | 988.6 | 1328.2 | 311.5 | 57.2 | 29.3 | |
| % Reduction in Shedding | 79.2 | 77.5 | 78.2 | 81.8 | 93.1 | 54.0 | 77.3 |
| P value[4] | 0.201 | 0.029* | 0.011* | 0.003** | 0.013* | 0.073 | 0.019* |
| P particle-VP8 (EDIM, N = 5) | | | | | | | |
| Mean antigen shedding | 5.4 | 575.3 | 662.4 | 875.6 | 139.0 | 9.2 | |
| Standard deviation | 12.0 | 1095.1 | 648.4 | 334.5 | 187.9 | 11.9 | |
| % Reduction in Shedding | 99.2 | 86.3 | 84.2 | 80.4 | 95.4 | 85.7 | 88.5 |
| P value[4] | 0.048* | 0.018* | 0.004** | 0.005** | 0.011* | 0.003** | 0.018* |

[1]Mice were immunized intranasally as described in Materials and Methods. Two weeks after the last immunization mice were challenged with 10[5] Shedding Dose 50 of murine EDIM. Stools were collected from each mouse for 6 days after challenge and analyzed for the quantity of rotavirus antigen.
[2]Mean shedding per mouse per day in each group.
[3]Protection is the percent reduction in shedding compared to the control group, either by day or over the 6 days
[4]P values were calculated comparing to the control group (wild type P particle). A star symbol indicates statistically significant, while a double star symbol indicates statistically very significant.

Immunization with the P Particle-VP8 Chimera-Induced Antibody that Blocked Norovirus Binding to HBGAs.

The role of the P particle backbone in immune responses in mice was also examined following immunization with the P particle-VP8 (Wa) chimera. As expected, the chimera-induced antibody reacted strongly with norovirus VLPs and P particles as determined in EIAs (FIG. 20A, data not shown). These sera also blocked norovirus VLP binding to HBGA receptor (Type A saliva, FIG. 20B). As a negative control, sera from animals immunized with the free VP8 (Wa) did not show such blockade. This result indicates that the P particle-VP8 chimera could be a dual vaccine against both rotavirus and noroviruses.

Our previous studies showed that the norovirus P particle is easily produced, extremely stable and highly immunogenic which can be used as a subunit vaccine against noroviruses. We have further demonstrated that the P particle can also be used as a novel vaccine platform for immune enhancement of a foreign antigen. We have shown that: 1) the surface loops of the P particle are excellent sites for foreign antigen insertion without affecting the formation and production of the P particle, 2) the P particle tolerates a foreign antigen in a size up at least to 159 amino acids, 3) the enhanced immune responses to inserted antigens have been demonstrated by both in vitro and in vivo neutralization and protection experiments. The P particle-VP8 chimera also provided a promising dual vaccine against both rotavirus and norovirus. Thus, the simple procedure to generate chimeric particles and the multiple surface loops with potential for multi-polyvalent foreign insertion make the P particle an attractive vaccine platform for antigen presentation for infectious diseases or other conditions that would benefit from an efficient vaccine.

A primary goal of the present invention is to examine whether the P particle can enhance immunogenicity of a small polypeptide antigen that is generally less immunogenic. We studied this issue using the His-tag as a model and obtained excellent results. Two major factors may be responsible for the observed immune enhancement, multi-copy number and surface exposure of the inserted antigens. The P particle is composed of 24 copies of P monomers, which may explain its enhanced immune responses comparing with the His-tag fused to a P dimer (FIG. 15A). The importance of surface exposure of the antigen was showed by the low immune responses to the two unexposed peptides that were linked to the N- or C-terminus of the P domain (FIGS. 15B and C). Thus, the P particle may act as an adjuvant by its large size (830 kDa) and proper presentation of a foreign antigen that otherwise has low immunogenicity. The increased multi-copy of an antigen per particle is another feature that may explain the increased immune responses.

In addition to the His-tag peptide, we have successfully inserted a number of other small peptides onto the P particles, including the T cell epitope of murine cytomegalovirus (9 aa), the Epi8 epitope of *Pseudomonas* (14 aa) and the M2 extracellular epitope of influenza A (23 aa) (Tan and Jiang, unpublished). These data suggested that the P particle may be readily useful for immune enhancement for a wide variety of small polypeptide antigens. The successful insertion of different rotavirus VP8s into P particles has greatly extended the application of the P particle platform for a wider range of larger foreign antigens. The rotavirus VP8 is a spike protein on the viral capsid and is believed to be important for rotavirus infectivity. It is also one of two antigens that induce neutralizing antibodies. A number of neutralizing epitopes have been identified on the VP8 protein. The success of the P particle-VP8 chimera to induce a neutralizing antibody response and provide protection against rotavirus shedding in mice suggested that these epitopes have been preserved on the P particle carrier.

While the two recently introduced rotavirus vaccines are highly effective, new generation vaccines may be needed for potentially new emerging viruses. Non-infectious subunit vaccines do not have a risk of reversion to virulent strains that may be a concern with the current vaccines. The development of a VLP vaccine for rotaviruses has been proposed for years. Rotavirus VLP vaccine have the challenge of low efficiency expression and high cost of manufacturing because of the requirement for co-transfection of several capsid genes to the baculovirus host. In contrast, generation of the P particle-VP8 chimera requires only a routine *E. coli*-based cloning and expression procedure, which is highly efficient and low in cost. In addition, cross-neutralization epitopes have been described on VP8. We have shown in this paper that immunization of mice with a chimeric P particle containing VP8 from a P[4] virus had cross neutralization against a P[8] rotavirus. A cocktail vaccine containing minimal number of P types may also be cost effective.

The ability of antibodies induced by the P particle-VP8 chimera to block the binding of norovirus VLPs to HBGAs is unexpected. As shown in FIG. 1, the distal surface of the P dimers, including the HBGA binding interfaces of the P particle is most likely to be covered by the inserted VP8s. This leads to the loss of the binding capability of the chimera to HBGA receptors (data not shown). One possibility for the continued blocking ability seen, is that the epitopes of the HBGA binding interfaces of the P particle-VP8 chimera are still accessible for antibody induction even thought they are covered by the inserted VP8 antigens. Alternatively, the observed carbohydrate blockage may be due to an antibody binding in the vicinity of the carbohydrate binding site. No matter which mechanism is involved, the ability of the chimera-induced antibody to block norovirus VLP binding to HBGAs adds an additional value to the P particle platform. The concept of a dual vaccine of the P particle-VP8 chimeric against both norovirus and rotavirus may be particularly valuable for specific populations at risk for both infections.

Although only loop 2 was examined in this study, the likelihood of success for antigen insertion in the other two loops are expected and is now being tested in our laboratory. The availability of three surface loops per P monomer provides opportunities for versatile vaccine designs. For example, to increase immune responses, the same epitope or antigen can be inserted in all three loops to reach 72 copies of the antigens per particle. Even higher copy number can also be generated by insertion of tandem-repeats of individual antigens. Alternatively, different antigens can be inserted into each of the three loops, resulting in a multi-valent vaccine against different pathogens or for rotavirus, different VP8 antigens. Additional vaccine templates may also be generated by insertion of functional tags for different purposes. For example, insertion of a His-tag would further simplify the purification procedure. Special ligands or signal molecules may also be used to stimulate immune responses by targeting the vaccine to special organs, tissues or cells of the host.

A further application of the P particle platform is for production of antibodies against small peptides for research and diagnostic uses. A variety of disease biomarkers (mainly peptide epitopes) has been identified and antibodies against these biomarkers are important for diagnostic purpose. Small peptides can be easily inserted into a loop of the P particle by a simple procedure of DNA cloning. We have developed convenient P particle vectors containing cloning cassettes that would further facilitate the process. Following expression of the recombinant chimeric P particle in bacteria, high titer antibodies specific to the inserted peptide antigens can be induced by immunization of laboratory animals according to the establish procedure in this study. Antibody production in this way will avoid the costly steps of peptide synthesis and conjugation of the peptide to a macromolecule such as keyhole limpet hemocyanin (KLH) for immune enhancement. Since the norovirus P domain has a unique sequence that shares no homology with any other proteins, cross reactivity with other proteins should not be a concern. Thus the P particle vaccine platform can be used as a convenient tool for antibody production in many areas of biomedical research.

While the present invention has been illustrated by the description of embodiments thereof, and while the embodiments have been described in considerable detail, it is not intended to restrict or in any way limit the scope of the appended claims to such detail. Additional advantages and modifications will be readily apparent to those skilled in the art. The invention in its broader aspects is therefore not limited to the specific details, representative system and method, and illustrated examples shown and described. Accordingly, departures may be made from such details without departing from the scope or spirit of the invention.

What is claimed is:

1. A method of inducing an immune response in a mammal against a viral antigen, comprising the step of administering to the mammal an effective amount of an immunogenic composition comprising an antigen-P-particle consisting of 24 monomers, said P-particle including at least one antigen-P-domain monomer, wherein the antigen-P-particle can enhance the immunogenicity of the antigen as compared to said antigen along; wherein said at least one antigen P-domain monomer comprises a Norovirus (NOR) P-domain monomer having at least one surface loop and a foreign protein or polypeptide antigen inserted into said at least one surface loop.

2. The method according to claim 1, wherein the foreign protein or polypeptide antigen is rotovirus (RV) VP8 antigen, thereby forming a P-particle-VP8 chimera, which serves as an immunogenic composition against both rotavirus and norovirus.

* * * * *

UNITED STATES PATENT AND TRADEMARK OFFICE
CERTIFICATE OF CORRECTION

PATENT NO. : 9,096,644 B2  
APPLICATION NO. : 13/924906  
DATED : August 4, 2015  
INVENTOR(S) : Ming Tan and Xi Jiang Page 1 of 1

It is certified that error appears in the above-identified patent and that said Letters Patent is hereby corrected as shown below:

In the Claims

Column 39, Claim 1, line 8, reads "said antigen along;" which should be deleted and replaced with "said antigen alone;"

Signed and Sealed this
First Day of December, 2015

Michelle K. Lee
*Director of the United States Patent and Trademark Office*